United States Patent
Yaver et al.

(10) Patent No.: US 9,150,856 B2
(45) Date of Patent: Oct. 6, 2015

(54) PROMOTER VARIANTS FOR EXPRESSING GENES IN A FUNGAL CELL

(71) Applicant: Novozymes, Inc., Davis, CA (US)

(72) Inventors: Debbie Yaver, Davis, CA (US); Peter Nham, Sacramento, CA (US)

(73) Assignee: NOVOZYMES, INC., Davis, CA (US)

( * ) Notice: Subject to any disclaimer, the term of this patent is extended or adjusted under 35 U.S.C. 154(b) by 9 days.

(21) Appl. No.: 14/097,659

(22) Filed: Dec. 5, 2013

(65) Prior Publication Data

US 2014/0099669 A1    Apr. 10, 2014

Related U.S. Application Data

(62) Division of application No. 13/424,018, filed on Mar. 19, 2012, now Pat. No. 8,604,181, which is a division of application No. 12/054,125, filed on Mar. 24, 2008, now Pat. No. 8,138,325, which is a division of application No. 10/716,793, filed on Nov. 18, 2003, now Pat. No. 7,368,262.

(60) Provisional application No. 60/427,314, filed on Nov. 18, 2002.

(51) Int. Cl.
| C12P 21/00 | (2006.01) |
| C12N 15/113 | (2010.01) |
| C12N 15/80 | (2006.01) |
| C12P 1/02 | (2006.01) |

(52) U.S. Cl.
CPC .............. *C12N 15/113* (2013.01); *C12N 15/80* (2013.01); *C12P 1/02* (2013.01); *C12P 21/00* (2013.01)

(58) Field of Classification Search
None
See application file for complete search history.

(56) References Cited

U.S. PATENT DOCUMENTS

| 5,837,847 A | 11/1998 | Royer et al. |
| 6,361,973 B1 | 3/2002 | Berka et al. |

FOREIGN PATENT DOCUMENTS

| WO | 96/00787 A1 | 1/1996 |
| WO | 97/26330 A2 | 7/1997 |
| WO | 00/56900 A2 | 9/2000 |

OTHER PUBLICATIONS

Ballance, James, 1991, Delta Biotechnology Limited, Nottingham, England, p. 1-29.
Minetoki et al 1996, Curr Genet 30 (5), 432-43.
Berka et al., 2000, Genbank, Accession No. AAF14787.

*Primary Examiner* — Michele K Joike
(74) *Attorney, Agent, or Firm* — Robert L. Starnes

(57) ABSTRACT

The present invention relates to methods for producing a biological substance, comprising: (a) cultivating a fungal host cell in a medium conducive for the production of the biological substance, wherein the fungal host cell comprises a first nucleic acid sequence encoding the biological substance operably linked to a second nucleic acid sequence comprising a promoter variant selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12; and a subsequence thereof; and hybrid and tandem promoters thereof; and (b) isolating the biological substance from the cultivation medium. The present invention also relates to the isolated promoter variants and to constructs, vectors, and fungal host cells comprising the promoter variants operably linked to nucleic acid sequences encoding biological substances.

14 Claims, 8 Drawing Sheets

Fig. 1A

```
accaacccaa aaacagacca actactcaca aaaaggcatc tcatcaagaa aaaacggcca 1740
actaacgtcc aaaaggcccg aaaaacgtcc atcacgccgc agccgagact tcaatagact 1800
gcacaagaag gaccgatgag atcgaccaga ctaaaccogg gagagtgtca aatatgcggg 1860
ggattgggga acttacccca gaaagagaga ggaggataaa ttccatgtct ggggttgacg 1920
tctctattgg ttagacacga acgcctgctc tcggcgtaat ttataccata gcgccaatga 1980
gggcggaaac tctgttttg tcaagtcgtc attgttggtt gggtcatgat atatagccag 2040
taggtatccg tcttggtgat tgaccagaca tatcgctcat cacagatcaa catcactgct 2100
atcaccaaca tg                                                      2112
```

PROMOTER VARIANTS FOR EXPRESSING GENES IN A FUNGAL CELL

CROSS-REFERENCE TO RELATED APPLICATIONS

This application is a divisional of U.S. application Ser. No. 13/424,018, filed Mar. 19, 2012, now U.S. Pat. No. 8,604,181, which is a divisional of U.S. application Ser. No. 12/054,125, filed Mar. 24, 2008, now U.S. Pat. No. 8,138,325, which is a divisional of U.S. application Ser. No. 10/716,793, filed Nov. 18, 2003, now U.S. Pat. No. 7,368,262, which claims priority from U.S. provisional application Ser. No. 60/427,314, filed Nov. 18, 2002, which applications are fully incorporated herein by reference.

BACKGROUND OF THE INVENTION

1. Field of the Invention

The present invention relates to methods for producing biological substances. The present invention also relates to isolated promoter variants and to nucleic acid constructs, vectors, and host cells comprising the promoter variants operably linked to nucleic acid sequences encoding biological substances.

2. Description of the Related Art

The recombinant production of a native or heterologous biological substance in a fungal host cell, particularly a filamentous fungal cell such as *Aspergillus*, may provide for a more desirable vehicle for producing the substance in commercially relevant quantities.

Recombinant production of a native or heterologous biological substance is accomplished by constructing an expression cassette in which the DNA coding for the protein is placed under the expression control of a promoter, excised from a regulated gene, suitable for the host cell. The expression cassette is introduced into the host cell, usually by plasmid-mediated transformation. Production of the substance is then achieved by culturing the transformed host cell under inducing conditions necessary for the proper functioning of the promoter contained on the expression cassette.

The development of a new fungal host cell for the recombinant production of biological substances generally requires the availability of promoters that are suitable for controlling the expression of the substances in the host cell. *Fusarium venenatum* has been shown to be useful as a new host cell for such expression (WO 96/00787, WO 97/26330). Moreover, the promoter from the *Fusarium oxysporum* trypsin-like protease gene has been described which is useful for expressing heterologous genes in *Fusarium venenatum* host cells (U.S. Pat. No. 5,837,847). U.S. Pat. No. 6,361,973 discloses a glucoamylase promoter from *Fusarium venenatum*. However, there is a need in the art for new promoters for controlling the expression of native and heterologous genes.

It is an object of the present invention to provide improved methods for producing a biological substance in a fungal host cell and new promoter variants for such production.

SUMMARY OF THE INVENTION

The present invention relates to methods for producing a biological substance, comprising: (a) cultivating a fungal host cell in a medium conducive for the production of the biological substance, wherein the fungal host cell comprises a first nucleic acid sequence encoding the biological substance operably linked to a second nucleic acid sequence comprising a promoter variant having a nucleic acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12; and subsequences thereof; and hybrid and tandem promoters thereof; and (b) isolating the biological substance from the cultivation medium. The biological substance may be native or heterologous to the fungal host cell.

The present invention also relates to isolated promoter variants comprising a nucleic acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12; and subsequences thereof; and hybrid and tandem promoters thereof; and to constructs, vectors, and fungal host cells comprising one or more of the promoter variants operably linked to a nucleic acid sequence encoding a biological substance.

BRIEF DESCRIPTION OF THE FIGURES

FIGS. 1A and B show the DNA sequence of the *Fusarium venenatum* native glucoamylase gene promoter sequence (SEQ ID NO: 1).

DETAILED DESCRIPTION OF THE INVENTION

Figure 2:
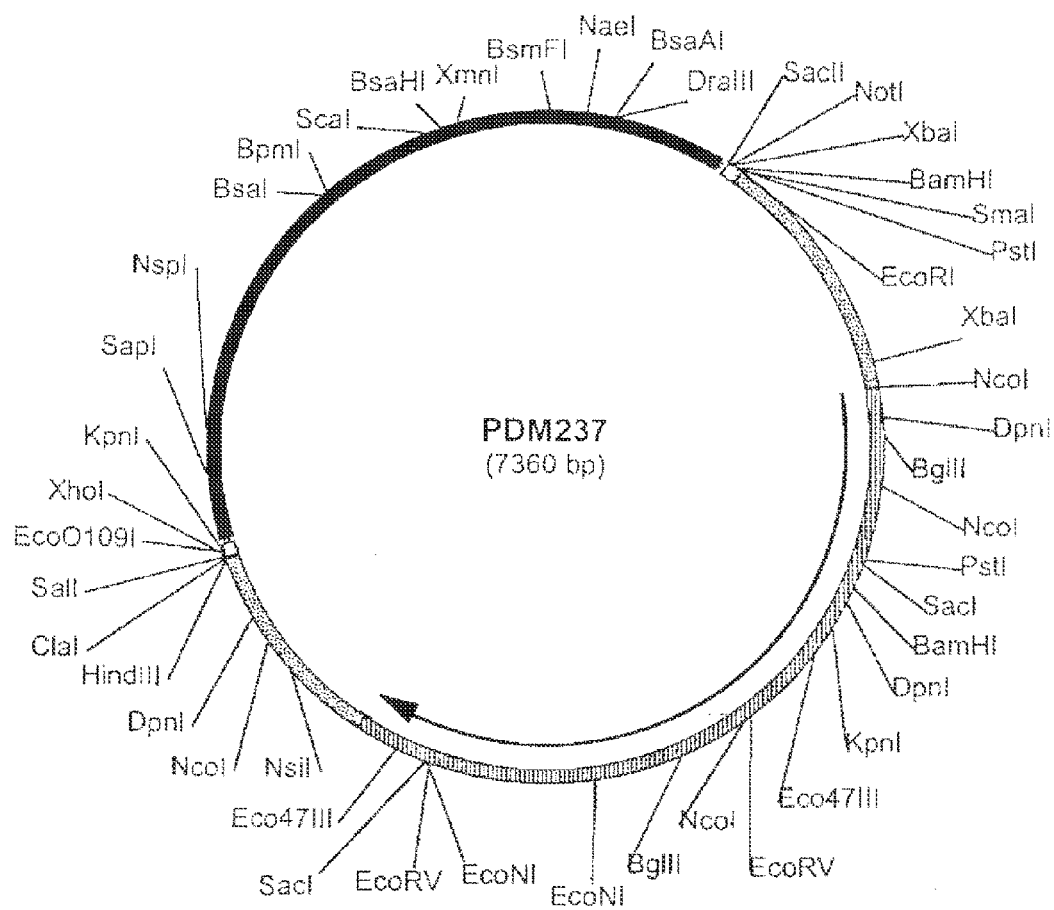
FIG. 2 shows a restriction map of pDM237.

The present invention relates to methods for producing a biological substance, comprising (a) cultivating a fungal host cell in a medium conducive for the production of the biological substance, wherein the fungal host cell comprises a first nucleic acid sequence encoding the biological substance operably linked to a second nucleic acid sequence comprising a promoter variant selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12; and subsequences thereof; and hybrid and tandem promoters thereof; and (b) isolating the biological substance from the cultivation medium.

In the production methods of the present invention, the cells are cultivated in a nutrient medium suitable for production of the biological substance using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the biological substance is secreted into the nutrient medium, the substance can be recovered directly from the medium. If the biological substance is not secreted, it can be recovered from cell lysates.

The biological substances may be detected using methods known in the art that are specific for the biological substances. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

The resulting biological substance may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). A metabolite of interest may be isolated from a cultivation medium by, for example, extraction, precipitation, or differential solubility, or any method known in the art. The isolated metabolite may then be further purified using methods suitable for metabolites.

Promoters

The term "promoter" is defined herein as a DNA sequence that binds RNA polymerase and directs the polymerase to the correct downstream transcriptional start site of a nucleic acid sequence encoding a biological substance to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

The term "promoter variant" is defined herein as a promoter having a nucleotide sequence comprising a substitution, deletion, and/or insertion of one or more nucleotides of a parent promoter, wherein the mutant promoter has more or less promoter activity than the corresponding parent promoter. The term "promoter variant" will also encompass natural variants and in vitro generated variants obtained using methods well known in the art such as classical mutagenesis, site-directed mutagenesis, and DNA shuffling.

The term "hybrid promoter" is defined herein as parts of two more promoters that are fused together to generate a sequence that is a fusion of the two or more promoters, which when operably linked to a coding sequence mediates the transcription of the coding sequence into mRNA.

The term "tandem promoter" is defined herein as two or more promoter sequences each of which is operably linked to a coding sequence and mediates the transcription of the coding sequence into mRNA.

The term "operably linked" is defined herein as a configuration in which a control sequence, e.g., a promoter sequence, is appropriately placed at a position relative to a coding sequence such that the control sequence directs the production of a biological substance encoded by the coding sequence.

The term "coding sequence" is defined herein as a nucleic acid sequence that is transcribed into mRNA which is translated into a biological substance, e.g., polypeptide, when placed under the control of the appropriate control sequences. The boundaries of the coding sequence are generally determined by the ATG start codon located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences.

A promoter variant of the present invention may have one or more mutations. Each mutation is an independent substitution, deletion, and/or insertion of a nucleotide. The introduction of a substitution, deletion, and/or insertion of a nucleotide into the promoter may be accomplished using any of the methods known in the art such as classical mutagenesis, site-directed mutagenesis, or DNA shuffling. Particularly useful is a procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl which is specific for methylated and hemimethylated DNA to digest the parental DNA template and to select for mutation-containing synthesized DNA. Other procedures known in the art may also be used.

Figure 1A:
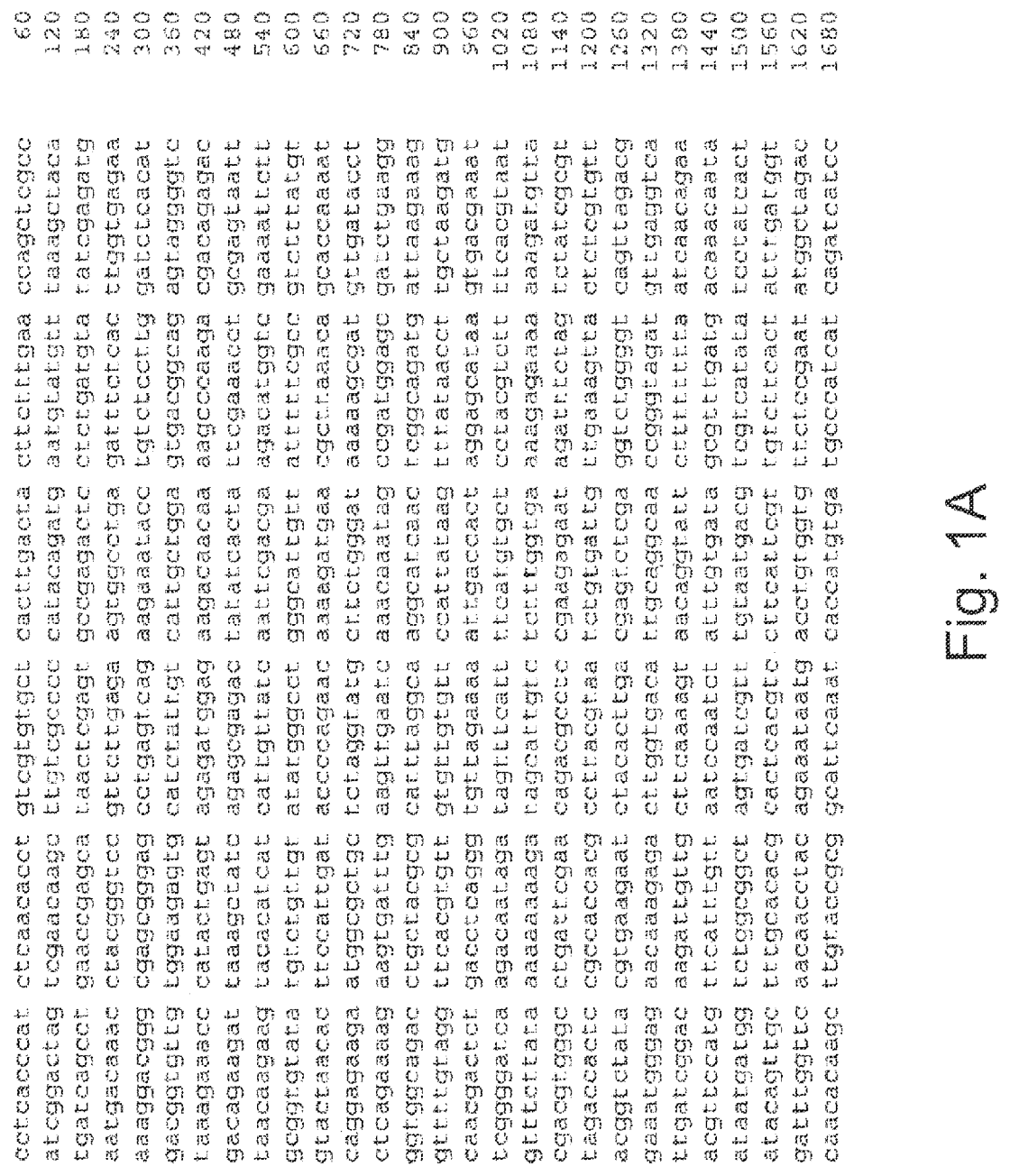

The parent promoter of the promoter variants of the present invention is SEQ ID NO: 1 shown in FIGS. 1A and 1B, or the nucleic acid sequence contained in plasmid pECO3 which is contained in *Escherichia coli* NRRL B-30067.

The regions chosen for deletion, insertion or substitution of SEQ ID NO: 1 were based on observations made about the nucleotide sequence of the *Fusarium venenatum* glucoamylase promoter. At positions, 3792 to 3807, 3678 to 3693, and 3814 to 3824 of SEQ ID NO: 1 (U.S. Pat. No. 6,361,973), there are regions that share homology to motifs found in other starch inducible fungal promoters. The regions were similar in sequence to the IIIa and IIIb regions described previously in *Aspergillus* amylase promoters (Minetoki et al., 1996, *Current Genetics* 30: 432-438). Region IIIa was found in the *Aspergillus oryzae* alpha-glucosidase, amylase B and glucoamylase promoters as well as in *Aspergillus niger* alpha-glucosidase promoter. Region IIIb was found only in the *Aspergillus niger* and *Aspergillus oryzae* alpha-glucosidase promoters. The 3792 to 3807 and 3678 to 3693 regions of the *Fusarium venenatum* glucoamlyase promoter have some sequence similarity to the Region IIIa consensus while the 3814 to 3824 has homology to the IIIb sequence. The analysis of the *Aspergillus* promoters by Minetoki et al. suggested that IIIa region was required for high level expression in the presence of starch or maltose while IIIb region was required for high level expression but does not play a role in starch induction. Minetoki et al. further demonstrated that a significant increase in promoter activity could be observed by introducing multiple copies of region IIIa into the *Aspergillus oryzae* alpha-glucosidase promoter. In the present invention, variants of the *Fusarium venenatum* glucoamylase promoter were constructed which demonstrated that the putative IIIa and IVb regions were important for expression. In addition, adding IIIa region 35 bp downstream of the 3792 to 3807 region improved the promoter. However, the IIIa consensus found in *Aspergillus* promoters (Minetoki et al., 1996, supra) was not as efficient as the native *Fusarium venenatum* IIIa promoter sequence.

In a preferred embodiment, the promoter variant has the nucleic acid sequence of SEQ ID NO: 2, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 3, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 4, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 5, or a subsequence thereof. The subsequence preferably contains at least about 1200 nucleotides, more preferably at least about 1500 nucleotides, and most preferably at least about 1800 nucleotides.

In another preferred embodiment, the promoter variant comprises at least two copies, more preferably at least three copies, and most preferably at least four copies of the sequence CGGCGTAATTTCGGCC in the *Fusarium venenatum* glucoamylase promoter.

In another preferred embodiment, the promoter variant has the nucleic acid sequence of SEQ ID NO: 6, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 7, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 8, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 9, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 10, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 11, or a subsequence thereof. The subsequence preferably contains at least about 1200 nucleotides, more preferably at least about 1500 nucleotides, and most preferably at least about 1800 nucleotides.

In another preferred embodiment, the promoter variant has the nucleic acid sequence of SEQ ID NO: 12, or a subsequence thereof. The subsequence preferably contains at least about 1200 nucleotides, more preferably at least about 1500 nucleotides, and most preferably at least about 1800 nucleotides.

In a preferred embodiment of the methods of the present invention, the promoter variant, which increases expression of the nucleic acid sequence encoding a biological substance, is selected from the group consisting of SEQ ID NO: 2, SEQ ID NO: 3, SEQ ID NO: 4, SEQ ID NO: 5; and subsequences thereof.

In another preferred embodiment of the methods of the present invention, the promoter variant, which decreases expression of the nucleic acid sequence encoding a biological substance, is selected from the group consisting of SEQ ID NO: 6, SEQ ID NO: 7, SEQ ID NO: 8; SEQ ID NO: 9, SEQ ID NO: 10, SEQ ID NO: 11, and SEQ ID NO: 12; and subsequences thereof.

In the methods of the present invention, the promoter variant may also be a hybrid promoter comprising a portion of one or more promoters of the present invention; a portion of a promoter of the present invention and a portion of another promoter, e.g., a leader sequence of one promoter and the transcription start site from the other promoter; or a portion of one or more promoters of the present invention and a portion of one or more other promoters. The other promoter may be any promoter sequence which shows transcriptional activity in the fungal host cell of choice including a mutant, truncated, and hybrid promoter, and may be obtained from genes encoding extracellular or intracellular polypeptides either homologous or heterologous to the host cell. The other promoter sequence may be native or foreign to the nucleic acid sequence encoding the biological substance and native or foreign to the cell.

Examples of other promoters useful in the construction of hybrid promoters with the promoter variants of the present invention include the promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei lipase, Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase), *Fusarium venenatum* Daria promote, *Fusarium venenatum* Quinn promoter, *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase; and mutant, truncated, and hybrid promoters thereof. Other useful promoters for yeast host cells are described by Romanos et al., 1992, *Yeast* 8: 423-488.

The promoter variant may also be a tandem promoter comprising two more promoter variants of the present invention or alternatively one or more promoter variants of the present invention and one or more other promoters, such as those exemplified above. The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the cell.

In the methods of the present invention, a hybrid or tandem promoter of the present invention will be understood to be foreign to a nucleic acid sequence encoding a biological substance even if the wild-type promoter is native to the nucleic acid sequence. For example, in a tandem promoter consisting of at least two promoters, one of the promoters may be a the wild-type promoter of the nucleic acid sequence encoding a biological substance.

A promoter variant of the present invention has at least about 20%, preferably at least about 40%, more preferably at least about 60%, more preferably at least about 80%, more preferably at least about 90%, more preferably at least about 100%, even more preferably at least about 200%, most preferably at least about 300%, and even most preferably at least about 400% of the promoter activity of the promoter of SEQ ID NO: 1.

Biological Substance Encoding Nucleic Acid Sequences

The biological substance encoded by the first nucleic acid sequence may be native or heterologous to the fungal host cell of interest. The biological substance may be any biopolymer or metabolite. The biological substance may be encoded by a single gene or a series of genes composing a biosynthetic or metabolic pathway or may be the direct result of the product of a single gene or products of a series of genes. Thus, the term "first nucleic acid sequence encoding a biological substance" will be understood to encompass one or more genes involved in the production of the biological substance. The term "heterologous biological substance" is defined herein as a biological substance which is not native to the host cell; or a native biological substance in which structural modifications have been made to alter the native biological substance.

In the methods of the present invention, the biopolymer may be any biopolymer. The term "biopolymer" is defined herein as a chain (or polymer) of identical, similar, or dissimilar subunits (monomers). The biopolymer may be, but is not limited to, a nucleic acid, polyamine, polyol, polypeptide (or polyamide), or polysaccharide.

In a preferred embodiment, the biopolymer is a polypeptide. The polypeptide may be any polypeptide having a biological activity of interest. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more may be heterologous to the fungal cell. Polypeptides further include naturally occurring allelic and engineered variations of the above-mentioned polypeptides and hybrid polypeptides.

In a preferred embodiment, the polypeptide is an antibody, antigen, antimicrobial peptide, enzyme, growth factor, hormone, immunodilator, neurotransmitter, receptor, reporter protein, structural protein, and transcription factor.

In a more preferred embodiment, the polypeptide is an oxidoreductase, transferase, hydrolase, lyase, isomerase, or ligase. In a most preferred embodiment, the polypeptide is an alpha-glucosidase, aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred embodiment, the polypeptide is a collagen or gelatin.

In another preferred embodiment, the biopolymer is a polysaccharide. The polysaccharide may be any polysaccharide, including, but not limited to, a mucopolysaccharide (e.g., heparin and hyaluronic acid) and nitrogen-containing polysaccharide (e.g., chitin). In a more preferred embodiment, the polysaccharide is hyaluronic acid.

In the methods of the present invention, the metabolite may be any metabolite. The metabolite may be encoded by one or more genes, such as a biosynthetic or metabolic pathway. The term "metabolite" encompasses both primary and secondary metabolites. Primary metabolites are products of primary or general metabolism of a cell, which are concerned with energy metabolism, growth, and structure. Secondary metabolites are products of secondary metabolism (see, for example, R. B. Herbert, *The Biosynthesis of Secondary Metabolites*, Chapman and Hall, New York, 1981).

The primary metabolite may be, but is not limited to, an amino acid, fatty acid, nucleoside, nucleotide, sugar, triglyceride, or vitamin.

The secondary metabolite may be, but is not limited to, an alkaloid, coumarin, flavonoid, polyketide, quinine, steroid, peptide, or terpene. In a preferred embodiment, the secondary metabolite is an antibiotic, antifeedant, attractant, bacteriocide, fungicide, hormone, insecticide, or rodenticide.

The nucleic acid sequence encoding a biological substance of interest may be obtained from any prokaryotic, eukaryotic, or other source. For purposes of the present invention, the term "obtained from" as used herein in connection with a given source shall mean that the biological substance is produced by the source or by a cell in which a gene from the source has been inserted.

The techniques used to isolate or clone a nucleic acid sequence encoding a biological substance of interest are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, PCR Protocols: A Guide to Methods and Application, Academic Press, New York. The cloning procedures may involve excision and isolation of a desired nucleic acid fragment comprising the nucleic acid sequence encoding the biological substance, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

Nucleic Acid Constructs

The present invention also relates to nucleic acid constructs comprising a nucleic acid sequence encoding a biological substance operably linked to at least one promoter variant of the present invention and one or more control sequences which direct the expression of the coding sequence in a suitable host cell under conditions compatible with the control sequences. Expression will be understood to include any step involved in the production of the biological substance including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleic acid sequence encoding a biological substance may be further manipulated in a variety of ways to provide for expression of the biological substance. Manipulation of the nucleic acid sequence prior to its insertion into a vector may be desirable or necessary depending on the expression vector. The techniques for modifying nucleic acid sequences utilizing recombinant DNA methods are well known in the art.

In the methods of the present invention, the nucleic acid sequence may comprise one or more native control sequences or one or more of the native control sequences may be replaced with one or more control sequences foreign to the nucleic acid sequence for improving expression of the coding sequence in a host cell.

The term "control sequences" is defined herein to include all components which are necessary or advantageous for the expression of a biological substance of the present invention. Each control sequence may be native or foreign to the nucleic acid sequence encoding the biological substance. Such control sequences include, but are not limited to, a leader, polyadenylation sequence, propeptide sequence, promoter variant of the present invention, signal peptide sequence, and transcription terminator. At a minimum, the control sequences include a promoter variant of the present invention, and transcriptional and translational stop signals. The control sequences may be provided with linkers for the purpose of introducing specific restriction sites facilitating ligation of the control sequences with the coding region of the nucleic acid sequence encoding a biological substance.

The control sequence may be a suitable transcription terminator sequence, a sequence recognized by a host cell to terminate transcription. The terminator sequence is operably linked to the 3' terminus of the nucleic acid sequence encoding the biological substance. Any terminator which is functional in the fungal host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the biological substance. Any leader sequence that is functional in the host cell of choice may be used in the present invention.

Preferred leaders for filamentous fungal host cells are obtained from the genes for *Aspergillus oryzae* TAKA amylase, *Aspergillus nidulans* triose phosphate isomerase, *Fusarium venenatum* trypsin, and *Fusarium venenatum* glucoamylase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the fungal host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a fungal host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the biological substance relative to the growth of the host cell. Examples of regulatory systems are those which cause the expression of the gene to be turned on or off in response to a chemical or physical stimulus, including the presence of a regulatory compound.

In yeast, the ADH2 system or GAL1 system may be used. In filamentous fungi, the TAKA alpha-amylase promoter, *Aspergillus niger* glucoamylase promoter, *Aspergillus oryzae* glucoamylase promoter, and *Fusarium venenatum* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the biological substance would be operably linked with the regulatory sequence.

The present invention also relates to nucleic acid constructs for altering the expression of a gene encoding a biological substance which is endogenous to a host cell. The constructs may contain the minimal number of components necessary for altering expression of the endogenous gene. In one embodiment, the nucleic acid constructs preferably contain (a) a targeting sequence, (b) a promoter variant of the present invention, (c) an exon, and (d) a splice-donor site. Upon introduction of the nucleic acid construct into a cell, the construct inserts by homologous recombination into the cellular genome at the endogenous gene site. The targeting sequence directs the integration of elements (a)-(d) into the endogenous gene such that elements (b)-(d) are operably linked to the endogenous gene. In another embodiment, the nucleic acid constructs contain (a) a targeting sequence, (b) a promoter variant of the present invention, (c) an exon, (d) a splice-donor site, (e) an intron, and (f) a splice-acceptor site, wherein the targeting sequence directs the integration of elements (a)-(f) such that elements (b)-(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670).

In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

The present invention further relates to methods for producing a biological substance comprising (a) cultivating a homologously recombinant cell, having incorporated therein a new transcription unit comprising a promoter variant of the present invention, an exon, and/or a splice donor site operably linked to a second exon of an endogenous nucleic acid sequence encoding the biological substance, under conditions conducive for production of the biological substance; and (b) recovering the biological substance. The methods are based on the use of gene activation technology, for example, as described in U.S. Pat. No. 5,641,670.

Expression Vectors

The present invention also relates to recombinant expression vectors comprising a promoter variant of the present invention, a nucleic acid sequence encoding a biological substance, and transcriptional and translational stop signals. The various nucleic acid and control sequences described above may be joined together to produce a recombinant expression vector which may include one or more convenient restriction sites to allow for insertion or substitution of the promoter and/or nucleic acid sequence encoding the biological substance at such sites. Alternatively, the nucleic acid sequence may be expressed by inserting the nucleic acid sequence or a nucleic acid construct comprising the promoter variant and/or sequence into an appropriate vector for expression. In creating the expression vector, the coding sequence is located in the vector so that the coding sequence is operably linked with a promoter variant of the present invention and one or more appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*. Preferred for use in a *Fusarium* cell is the bar, amdS, pyrG, or hygB gene.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the biological substance or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of a plasmid replicator useful in a yeast cell are the 2 micron origin of replication, ARS1, ARS4, the combination of ARS1 and CEN3, and the combination of ARS4 and CEN6. Examples of a plasmid replicator useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a biological substance may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a promoter variant of the present invention operably linked to a nucleic acid sequence encoding a biological substance, which are advantageously used in the recombinant production of the biological substances. A vector comprising a promoter variant of the present invention operably linked to a nucleic acid sequence encoding a biological substance is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the biological substance and its source.

The host cell may be any fungal cell useful in the methods of the present invention. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series NO:* 9, 1980).

In a more preferred embodiment, the yeast host cell is a *Candida*, *Hansenula*, *Kluyveromyces*, *Pichia*, *Saccharomyces*, *Schizosaccharomyces*, or *Yarrowia* cell.

In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma.*

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

In an even most preferred embodiment, the *Fusarium venenatum* cell is *Fusarium* venenatum A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium* venenatum ATCC 20334, as disclosed in WO 97/26330.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The present invention is further described by the following examples which should not be construed as limiting the scope of the invention.

EXAMPLES

Chemicals used as buffers and substrates were commercial products of at least reagent grade.
Strains and Materials Fungal strains used in the present invention were *Fusarium venenatum* wild-type strain MLY3 (see U.S. Pat. Nos. 6,066, 493 and 6,180,366) and pyrG mutant strain, *Fusarium venenatum* DLM15. Bacterial strains used to generate plasmids were *Escherichia coli* Top 10 (Invitrogen, Carlsbad, Calif.), Epicurian *E. coli* XL1 Blue competent and supercompetent cells (Stratagene, La Jolla, Calif.), and *E. coli* SEDM1 HKA702 (Stratagene, La Jolla, Calif.).

RA medium was composed per liter of 50 g of succinic acid, 4.9 g of urea, 1 g of glucose, and 20 ml of 50× Vogels salts.

50× Vogel's Salts was composed per liter of 150 g of sodium citrate, 250 g of $KH_2PO_4$, 10 g of $MgSO_4$-$7H_2O$, 20 ml of 25% $CaCl_2$.$2H_2O$, 5.0 ml of biotin (5 mg per 100 ml of 50% ethanol), and 5 ml of Vogels trace elements (filter sterilized).

Vogel's trace elements solution was composed per liter of 50 g of citric acid, 50 g of $ZnSO_4$.$7H_2O$, 10 g of $Fe(NH_4)_2(SO_4)_2$.$6H_2O$, 2.5 g of $CuSO_4$.$5H_2O$, 0.5 g of $MnSO_4$.$H_2O$, 0.5 g of $H_3BO_3$, and 0.5 g of $Na_2MoO_4$.$2H_2O$.

Minimal medium transfer and transformation plates (pH 6.5) were composed per liter of 6 g of $NaNO_3$, 0.52 g of KCL, 1.52 g of $KH_2PO_4$, 1 ml of Cove trace elements, 20 grams of Noble agar with addition of 20 ml of 50% glucose, 2.5 ml of 20% $MgSO_4$.7H2O and 20 ml of 0.02% biotin after autoclaving. Transformation plates contained all of the above ingredients plus sucrose at a final concentration of 0.8 M.

Cove trace elements solution was composed per liter of 0.04 g of $Na_2B_4O_7$.$10H_2O$, 0.4 g of $CuSO_4$.$5H_2O$, 1.2 g of $FeSO_4$.$7H_2O$, 0.7 g of $MnSO_4$.$H_2O$, 0.8 g of $Na_2MoO_2$.$2H_2O$, and 10 g of $ZnSO_4$.$7H_2O$.

Vogels $NH_4H_2PO_4$ plates were composed per liter of 20 ml of 50× Vogels salts, 15 g of sucrose, 25 g of Noble agar with addition of 50 ml of $NH_4H_2PO_4$ (1 M pH 6) after autoclaving.

M400 medium (pH 6) was composed per liter of 50 g of maltodextrin, 2 g of $MgSO_4$.$7H_2O$, 2 g $KH_2PO_4$, 4 g of citric acid, 8 g of yeast extract, 2 g of urea, 0.5 ml of AMG trace elements, and 0.5 g of $CaCl_2$.

AMG trace elements solution was composed per liter of 14.3 g of $ZnSO_4$.$7H_2O$, 2.5 g of $CuSO_4$.$5H_2O$, 0.5 g of $NiCl_2$.$6H_2O$, 13.8 g of $FeSO_4$.$7H_2O$, 8.5 g of $MnSO_4$.$H_2O$, and 3 g of citric acid.

Chlorate plates were composed per liter of 20 ml of Cove salt solution, 61.28 g of potassium chlorate, 0.3 g of urea, and 25 g of Noble agar.

Cove salt solution was composed per liter of 26 g of KCl, 26 g of $MgSO_4$.$7H_2O$, 76 g of $KH_2PO_4$, and 50 ml of Cove trace elements solution.

LB plus ampicillin broth was composed per liter of 10 g of tryptone, 5 g of yeast extract, 5 g of sodium chloride, and 100 mg of ampicillin.

LB plus ampicillin plates were composed of 1 liter of LB plus ampicillin broth with 15 g of bacto agar.

YP-5% glucose broth was composed per liter of 10 g of yeast extract, 20 g of bacto peptone, and 5% glucose.

2XYT plus ampicillin was composed per liter of 16 g of tryptone, 10 g of yeast extract, 5 g of sodium chloride, and 100 mg of ampicillin.

2XYT plus ampicillin plates were composed per liter of 2XYT+ ampicillin broth plus 15 g of bacto agar.

NYZ plus broth (pH 7.5) was composed per liter of 5 g of NaCl, 2 g of $MgSO_4$.$7H_2O$, 5 g of yeast extract, 10 g of NZ amine (casein hydrolysate), 12.5 ml of 1 M $MgCl_2$, 12.5 ml of 1 M $MgSO_4$, and 20 ml of 20% glucose.

NZY top agarose was composed per liter of 5 g of NaCl, 2 g of $MgSO_4$.$7H_2O$, 5 g of yeast extract, 10 g of NZ amine (casein hydrolysate), and 7 g of agarose.
DNA Sequencing DNA sequencing was done with a Perkin-Elmer Applied Biosystems Model 3700 Automatic DNA Sequencer (Perkin-Elmer Applied Biosystems, Inc., Foster City, Calif.) using dye-terminator chemistry (Giesecke et al., 1992, *Journal of*

Virology Methods 38: 47-60) and the reverse or forward lac sequencing primer or sequence specific primers.

Example 1

Construction of pDM237 pDM237 (FIG. 2) was constructed to contain a 4.4 kb EcoRI/HindIII *Fusarium venenatum* niaD fragment cloned into pBluescript SK(−) (Stratagene, La Jolla, Calif.). The niaD insert was composed of a 1.8 kb KpnI/EcoRI fragment from clone F (a genomic niaD clone) and a 2.6 kb KpnI/HindIII fragment from pDM201 (a genomic clone of niaD).

The niaD genomic clones were isolated from the Lambda ZipLox *Fusarium venenatum* genomic library described previously (U.S. Pat. No. 6,361,973). Clone pDM201 was isolated by probing the library with a 1.1 kb *Fusarium oxysporum* niaD fragment (Diolez et al., 1993, *Gene* 131: 61-67). The *Fusarium oxysporum* probe was amplified from *Fusarium oxysporum* genomic DNA using the following primers:

```
                                          (SEQ ID NO: 13)
5'-ATCGAGGGTGCCAATGTG-3' (foxy.nia1)

(SEQ ID NO: 14)
5'-GCCATTTACGACCTCAGC-3' (foxy.nia2).
```

The 100 µl PCR reaction contained 10 µg of genomic DNA, 50 pmol of each primer, 1× Taq buffer (Boehringer Mannheim, Indianapolis, Ind.), 200 µM each of dATP, dCTP, dGTP, and dTTP, and 5 units of Pwo DNA polymerase (Boehringer Mannheim, Indianapolis, Ind.). PCR conditions used were 95° C. for 3 minutes followed by 30 cycles at 95° C. for 30 seconds, 50° C. for 1 minute, and 72° C. for 1 minute. The final extension cycle was at 72° C. for 5 minutes. The PCR product was subcloned using the TA cloning kit from Invitrogen (Carlsbad, Calif.). The sublcones were checked by restriction digest with EcoRI and confirmed by nucleotide sequencing using the M13 universal forward and reverse primers. One of the clones was confirmed to contain the 1.1 kb niaD insert and was named pDM197.

To prepare a DIG-labeled probe of the *Fusarium oxysporum* niaD fragment, pDM197 was digested with EcoRI and a 1.1 kb fragment was isolated following gel electrophoresis on a 0.8% agarose gel using 40 mM Tris-acetate, 1 mM disodium EDTA buffer (TAE) and extraction of the DNA from the gel using the QIAquick Gel Extraction Kit (Qiagen, Inc., Chatsworth, Calif.). The probe was prepared by PCR using the primers foxy.nia1 and foxy.nia2 described above. The 100 µl PCR reaction contained 6 ng of 1.1 kb EcoRI niaD fragment, 50 pmol of each primer, 1× Taq buffer (Boehringer Mannheim, Indianapolis, Ind.), 10 µl of 10×DIG labeling mix (Boehringher Mannheim, Indianapolis, Ind.), and 5 units of Taq DNA polymerase (Boehringer Mannheim, Indianapolis, Ind.). PCR conditions used were 95° C. for 3 minutes followed by 30 cycles at 95° C. for 30 seconds, 50° C. for 1 minute, and 72° C. for 1 minute. The final extension cycle was at 72° C. for 5 minutes.

Approximately 90,000 plaques from the *Fusarium venenatum* genomic DNA library were screened by hybridization (Davis et al., 1986, *Basic Methods in Molecular Biology*, Elsevier Science Publishing Co., Inc., New York) with the DIG-labeled probe using medium stringency conditions [i.e., hybridization at 37° C. in DIG Easy hyb (Boehringher Mannheim, Germany); filters washed twice in 2×SSC with 0.1% SDS at room temperature for 5 minutes followed by two washes in 0.2×SSC with 0.1% SDS at the same temperature for 15 minutes)]. For detection of the DIG-labeled probe the standard Genius protocol from Boehringher Mannheim was followed using CPD Star as the substrate following the manufacturer's protocols. Plaques providing hybridization signals were purified twice on *E. coli* Y1090ZL cells, and the individual clones were subsequently excised from the λZipLox vector as pZL1-derivatives (D'Alessio et al., 1992, Focus® 14: 76). DNA sequence analysis revealed that one of these clones, containing a plasmid designated pDM201, contained the niaD gene, but was missing approximately 400 bp at the 5' end of the open reading frame.

In order to obtain a genomic clone containing the entire niaD open reading frame as well as the promoter, the genomic clone pDM201 was used to create a probe to a 0.46 kb fragment at the 5' end of the open reading frame. The probe was prepared by PCR using the following primers:

```
                                          (SEQ ID NO: 15)
5' CCCCGATAAAGATGGCTGTA 3' (niaprobe.plus)

(SEQ ID NO: 16)
5' TCGCTAGGCTCTTGGGTGAC 3' (niaprobe.minus)
```

The 50 µl PCR reaction contained 6 ng of pDM201, 50 pmol each primer, 1× Taq buffer (Boehringer Mannheim, Indianapolis, Ind.), 5 µl of 10×DIG labeling mix (Boehringher Mannheim, Indianapolis, Ind.), and 5 units of Taq DNA polymerase (Boehringer Mannheim, Indianapolis, Ind.). PCR conditions used were 95° C. for 3 minutes followed by 30 cycles at 95° C. for 30 seconds, 50° C. for 1 minute, and 72° C. for 1.5 minutes. The final extension cycle was at 72° C. for 5 minutes.

Approximately 80,000 plaques from the *Fusarium venenatum* genomic DNA library were screened by hybridization (Davis et al., 1986, supra) with the DIG-labeled probe using high stringency conditions (i.e., hybridization at 65° C. in DIG Easy hyb; filters washed twice in 2×SSC with 0.1% SDS at room temperature for 5 minutes followed by two washes in 0.1×SSC with 0.1% SDS at 65° C. for 15 mintutes). For detection of the DIG-labeled probe the standard Genius protocol from Boehringher Mannheim was followed using CPD Star as the substrate following the manufacturer's protocols. Plaques yielding hybridization signals were purified twice on *E. coli* Y1090ZL cells, and the individual clones were subsequently excised from the λZipLox vector as pZL1-derivatives. DNA sequence analysis revealed that one of these clones, containing a plasmid designated clone F, contained the niaD gene as well as 1.6 kb of the promoter. However, the clone was missing 450 bp at the 3' end of the open reading frame.

Plasmid pDM237 (FIG. 2), containing the entire niaD open reading frame as well as the promoter and terminator, was created. pDM237 consisted of a 4.4 kb EcoRI/HindIII *Fusarium venenatum* niaD fragment cloned into pBluescript SK(−) (Stratagene, La Jolla, Calif.) constructed as described below. The niaD insert consisted of a 1.8 kb KpnI/EcoRI fragment from clone F and a 2.6 kb KpnI/HindIII fragment from pDM201. Following restriction digests of pDM201 and clone F with KpnI/HindIII and KpnI/EcoRI; respectively, and electrophoresis on an agarose gel using TAE buffer, the desired fragments were isolated using a QIA quick gel extraction kit. The plasmid pBluescript SK(−) was digested with EcoRI/HindIII followed by electrophoresis and isolation as described above. The 2.9 kb pBluescript SK(−) plasmid was ligated with the 1.8 kb KpnI/EcoRI and the 2.6 kb KpnI/HindIII fragments for three hours at 14° C. followed by transformation of SURE competent cells from Stratagene (La Jolla, Calif.) selecting on 2XYT ampicillin plates. Plasmid DNA was isolated from clones, and the restriction analysis was used to confirm that the clone pDM237 contained the desired insert.

Example 2

Figure 3:
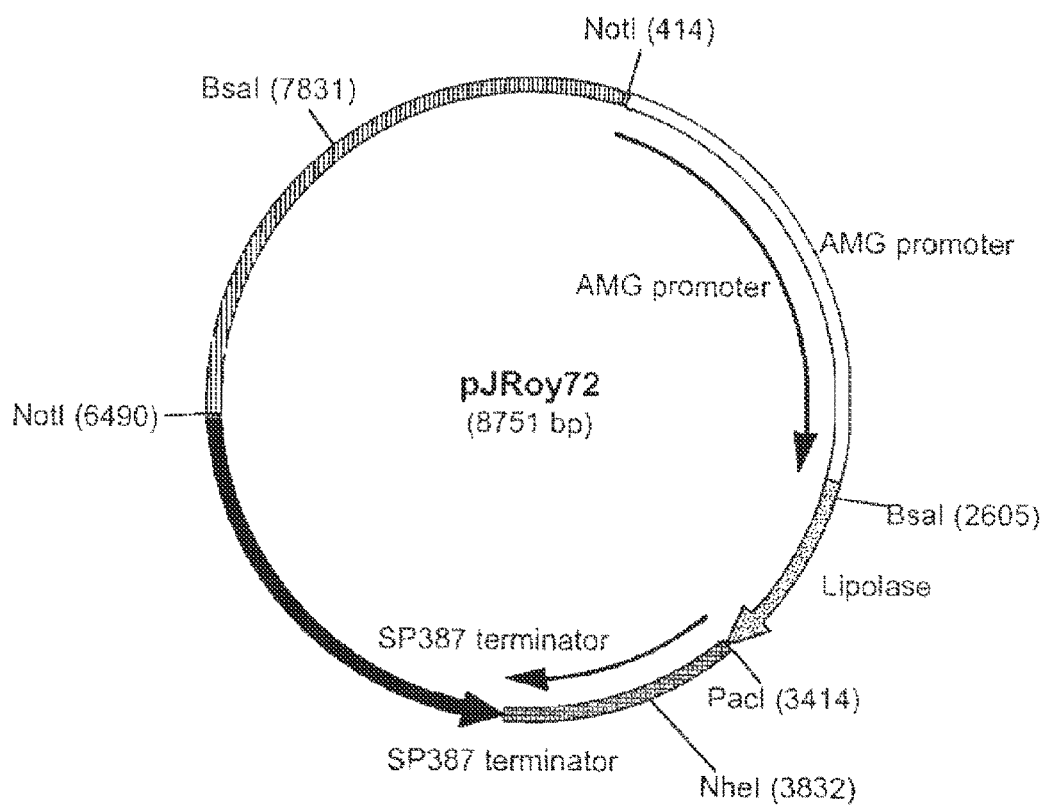
FIG. 3 shows a restriction map of pJRoy72.

Construction of pJRoy72 pJRoy72 (FIG. 3) was constructed by ligating a 0.9 kb PCR product containing a *Thermomyces lanuginosus* lipase gene, a 2.1 kb StuI/BspLU11I from pRaMB62-int1 (U.S. Pat. No. 6,361,973) and PmeI/PacI digested pRamB60 (U.S. Pat. No. 6,361,973). The lipase fragment was amplified from pDM194 (U.S. Pat. No. 6,361,973) using the following primers:

(SEQ ID NO: 17)
5'-GACTCATGAGGAGCTCCCTTGTGCTGTTC-3'

(SEQ ID NO: 18)
5'-TGATTAATTAACCTAAAGACATGTCCCAATTAAC-3'

The 100 µl PCR reaction contained 15 ng of pDM194, 50 pmol of each primer, 1×PCR buffer (Perkin-Elmer Corp., Branchburg, N.J.), 250 µM each of dATP, dCTP, dGTP, and dTTP, and 5 units of Pwo DNA polymerase (Boehringer Mannheim, Indianapolis, Ind.). The PCR conditions used were one cycle at 94° C. for two minutes, 10 cycles of 94° C. for 30 seconds, 55° C. for 45 seconds, and 72° C. for two minutes followed by 17 cycles at 94° C. for 30 seconds, 55° C. for 45 seconds, and 72° C. for two minutes with an extension of 20 seconds more for each cycle. The final cycle was 72° C. for 10 minutes. The 0.9 kb PCR product was ethanol precipitated followed by digestion with PacI and BspHI.

The PmeI/PacI digested pRaMB60, StuI/BspLU11I digested pRaMB62-int1 and 0.9 kb PCR product were electrophoresed on a 1% agarose gel using TAE buffer, and the DNA was purified from the excised band using a Qiaquick kit following the manufacturer's protocol.

To construct pJRoy72, the 5.8 kb PmeI/PacI fragment of pRaMB60 was ligated with the 0.9 kb PacI/BspHI lipase fragment and the 2.1 kb StuI/BspLU11I fragment from pRaMB62-int1. The resulting vector, pJRoy72 (FIG. 3), contained the *Thermomyces lanuginosus* lipase gene under the control of the *Fusarium venenatum* glucoamylase promoter (SEQ ID NO: 1).

Example 3

Construction of pNham1

Figure 4:
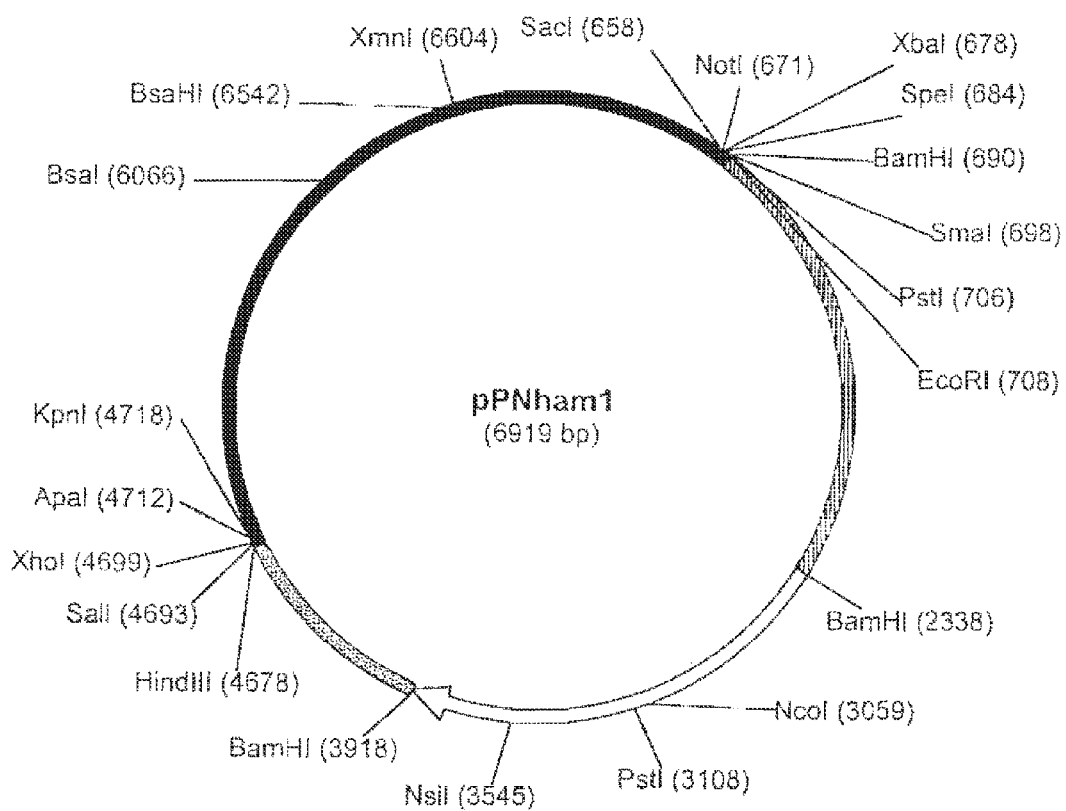
FIG. 4 shows a restriction map of pNham1.

Plasmid pNham1 (FIG. 4) was constructed using the following strategy: A 1.6 kb fragment containing the niaD promoter was isolated by digesting pDM237 with BamHI/EcoRI and a 760 bp fragment containing the niaD terminal region was isolated by digesting pNham3 of Example 5 with BamHI/HindIII. A fragment of approximately 1.6 kb containing the *Aspergillus oryzae* pyrG gene was obtained by digesting pSMO122 (U.S. Pat. No. 5,958,727) with BamHI. A 2.9 kb backbone vector fragment was generated by digesting pBluescript SK(−) with EcoRI and HindIII followed by treatment with shrimp alkaline phosphatase (Boehringer-Mannheim, Germany) to prevent self-ligation. After digestion, all the fragments were isolated by electrophoresis on a 0.7% agarose gel using TAE buffer followed by excision of the bands containing the desired fragments and isolation of the DNA from the gel using the Qiaquick Gel Extraction Kit following the manufacturer's protocol. All gel-purified fragments were ligated together to construct pNham1 using Rapid DNA Ligation Kit (Boehringer Mannheim, Germany) with the following ligation mix: 2 µl of BamHI/HindIII fragment from pNham3, 2 µl of BamHI/EcoRI fragment from pDM237, 2 µl of BamHI from pSMO122, 1 µl of pBluescript SK(−), 10 µl of 2× T4 DNA dilution buffer, 2 µl of 5×DNA dilution buffer, and 1 µl of T4 ligase. The ligation reaction was incubated at room temperature for 30 minutes. Epicurian *E. coli* XL Blue competent cells (Stratagene, La Jolla, Calif.) were transformed, and transformants were selected on 2XYT ampicillin plates. Plasmid DNA was isolated from several of the transformant colonies by inoculating a colony into 2.5 ml of LB medium supplemented with ampicillin (100 µg/ml). The tube was incubated at 37° C. for overnight with shaking at 250 rpm. Plasmid DNA was isolated using the Qiagen BioRobot following the manufacturer's protocols. The plasmids were analyzed by restriction enzyme digestion to confirm the correct inserts.

Example 4

Construction of pNham2

Figure 5:
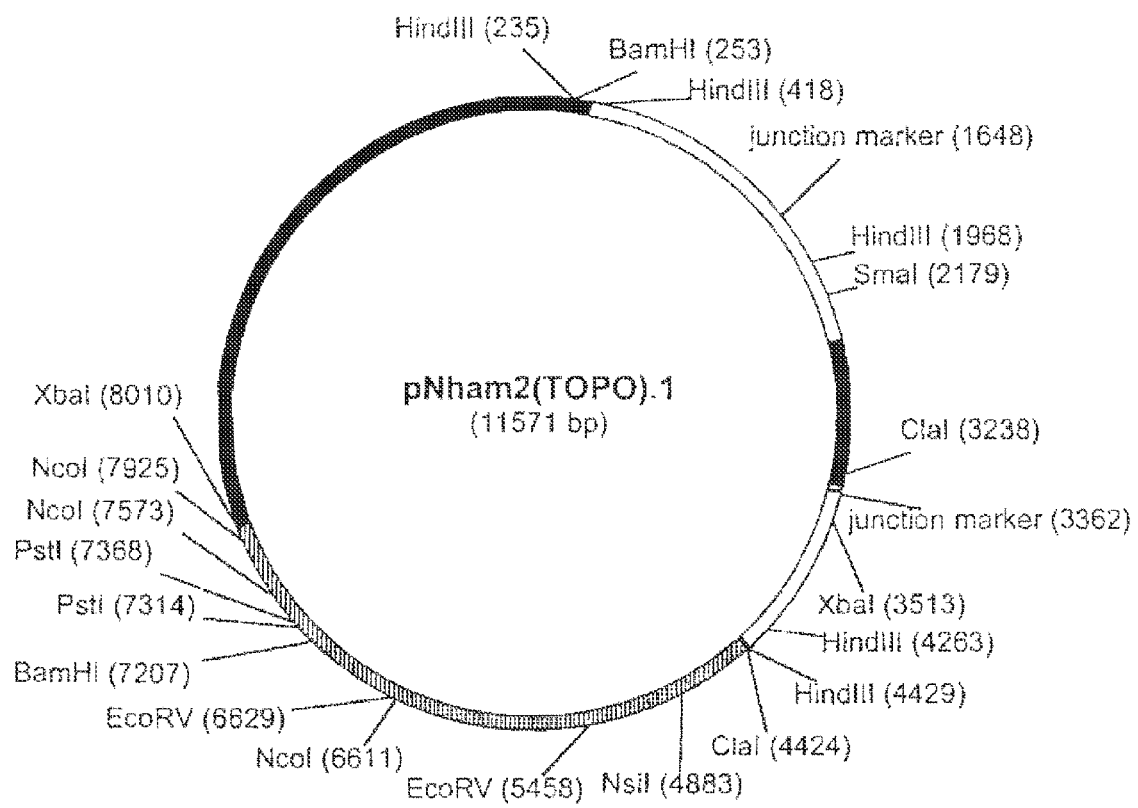
FIG. 5 shows a restriction map of pNham2.

Plasmid pNham2 (FIG. 5) was constructed to contain the truncated *Fusarium venenatum* niaD gene and an expression cassette where the *Thermomyces lanuginosus* lipase gene is sandwiched between the *Fusarium venenatum* glucoamylase promoter and the *Fusaium oxysporum* trypsin terminator. A 1.1 kb fragment containing the terminator of *Fusarium oxysporum* trypsin gene and a 3.0 kb fragment containing the *Thermomuyces lanuginosus* lipase/glucoamylase promoter regions were isolated by digesting pJRoy72 with PacI/ClaI and PacI/NotI, respectively. A 3.6 kb fragment containing a truncated niaD fragment was obtained by digesting pDM237 with XbaI/ClaI. A 3.9 kb fragment containing the backbone vector was prepared by digesting pCR2.1®-TOPO® (Invitrogen, Carlsbad, Calif.) with XbaI and NotI followed by treatment with shrimp alkaline phosphatase (Boehringer-Mannheim, Indianapolis, Ind.) to prevent self-ligation. After digestion all the fragments were isolated by electrophoresis on a 0.7% agarose gel using TAE buffer followed by excision of the bands containing the desired fragments and isolation of the DNA from the gel using the Qiaquick Gel Extraction Kit following the manufacturer's protocol.

pNham2 was obtained by ligation of 2 µl of the PacI/ClaI fragment from pJRoy72, 2 µl of the PacI/NotI fragment from pJRoy72, 2 µl of the XbaI/ClaI fragment from pDM237, 1 µl of the XbaI/NotI fragment from pCR2.1®-TOPO®, 1 µl of 10× ligation buffer, and 1 µl of T4 DNA ligase using the Rapid DNA Ligation Kit (Boehringer Mannheim, Germany). The ligation reaction was incubated at 14° C. for 24 hours. Epicurian *E. coli* XL blue competent cells (Stratagene, La Jolla, Calif.) were transformed, and transformants were selected on LB plates supplemented with 50 mg of ampicillin per liter. Plasmid DNA was isolated from several of the transformant colonies and analyzed by endonuclease digestion and by sequencing of pNham2 to confirm the sequence of the glucomylase promoter.

Example 5

Construction of pNham3

A 760 bp fragment of the BamHI/HindIII niaD terminator from pDM237 was amplified by PCR with the following primers:

5'-GGATCCTTGAATAAGCGTAAATAGGG-3' (SEQ ID NO: 19)

5'-AAGCTTGCTGAGCATTTGACTGCC-3' (SEQ ID NO: 20)

The PCR reaction contained 1 µl of 1:10 dilution of pDM237 (0.3 µg/µl-0.35 µg/µl), 5 µl of 10× Taq buffer (Perkin Elmer Corp., Branchburg, N.J.), 1 µl of 25 mM dNTPs (Boehringer Mannheim, Indianapolis, Ind.), 1 µl of 50 pmol primer 1, 1 µl of 50 pmol primer 2, 0.5 µl of 5 units/µl Taq polymearse (Perkin Elmer), and 40.5 µl of distilled water. The PCR reaction was performed in an Ericomp TwinBlock Thermal Cycler with the following cycling parameters and conditions: 1 cycle at 95° C. for 3 minutes followed by 25 cycles at 95° C. for 30 seconds, 55° C. for 30 seconds, and 72° C. for 1 minute followed by 1 cycle at 72° C. for 10 minutes. An aliquot of the PCR reaction was electrophoresed on a 1% agarose-TAE gel to verify the amplification of a 760 bp fragment.

The 760 bp PCR product of the *Fusarium venenatum* niaD terminator was cloned into pCRII using Topo TA cloning Kit (Invitrogen, Carlsbad, Calif.) following the manufacturer's protocol for cloning and transformation. Plasmid DNA was isolated from several of the transformants and sequence analysis was performed to confirm the clones that contain the 760 bp insert.

Example 6

Construction of *Fusarium venenatum* pyrG Mutant DLM15

A 0.78 kb fragment of the *Neurospora crassa* pyr-4 gene was labeled in a PCR reaction containing digoxigenin (DIG)-labeled deoxyuridine-triphosphate (dUTP) using the primers described below.

```
Primer 94-885 (sense):
5'-GTCAGGAAACGCAGCCACAC-3'      (SEQ ID NO: 21)

Primer 94-959 (anti-sense):
5'-AGGCAGCCCTTGGACGACAT-3'      (SEQ ID NO: 22)
```

A 1.1 kb HindIII fragment purified from plasmid pFB6 (Fungal Genetics Stock Center) was used as template. The PCR conditions for the Taq polymerase reaction were 95° C. for 3 minutes followed by 35 cycles of 95° C. for 30 seconds, 55° C. for 1 minute and 72° C. for 1 minute. A final extension was performed 5 minutes at 72° C. The DIG-labeled probe was used to screen a genomic library of *Fusarium venenatum* strain ATCC 20334 DNA cloned into lambda vector EMBL4 using the same procedure described in Royer et al., 1995, *Bio/Technology* 13: 1479-1483. Lambda phage were plated with *E. coli* K802 cells (Clonetech, Palo Alto, Calif.) onto LB plates with NZY top agarose. Plaque lifts were made to nylon membranes (Hybond™ membrane, Amersham Pharmacia Biotech, UK) using standard techniques. DNA was bound to the membranes by UV crosslinking. Filters were hybridized with the 0.78 kb DIG-labeled probe described above. Hybridization and detection of pyrG clones were performed using techniques described in the Boehringer Mannheim Genius™ System User's Guide. Hybridizations were performed at 42° C. in 5×SSC, 35% formamide, 0.1% L-lauroylsarcosine, 0.02% SDS, 1% blocking reagent for nucleic acid hybridization (Boehringer Mannheim, Indianapolis, Ind.). The concentration of DIG-labeled probe used was 2.5 ng per ml of hybridization solution. Hybridizing DNA was immunodetected with an alkaline-phosphatase-conjugated anti-digoxigenin antibody and visualized with Lumiphos 530, a chemiluminescent substrate (Boehringer Mannheim, Indianapolis, Ind.). DNA preparations were made from putative positive lambda clones using the Qiagen Lambda Midi Kit (QIAGEN, Inc., Chatsworth, Calif.).

Figure 6:
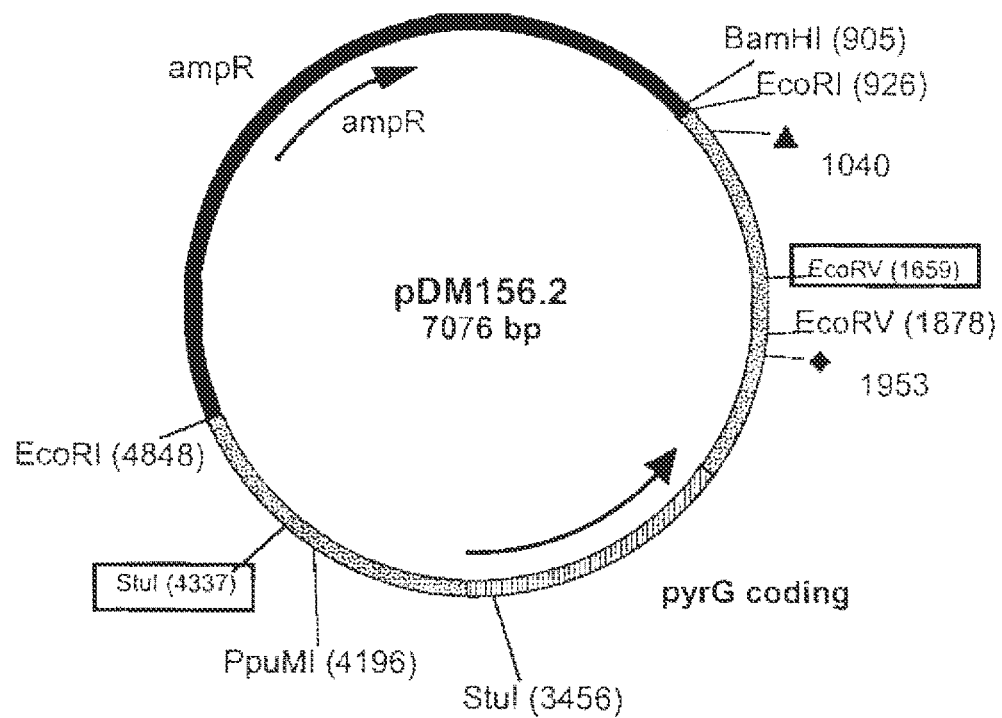
FIG. 6 shows a restriction map of pDM156.2.

A 3.9 kb genomic EcoRI pyrG fragment was gel purified from one of the lambda clones and cloned into the EcoRI site of pUC118 yielding plasmid pDM156.2 (FIG. 6). The pyrG fragment contained the entire coding region plus 1.3 kb of the promoter and 1.5 kb of the terminator.

Figure 7:
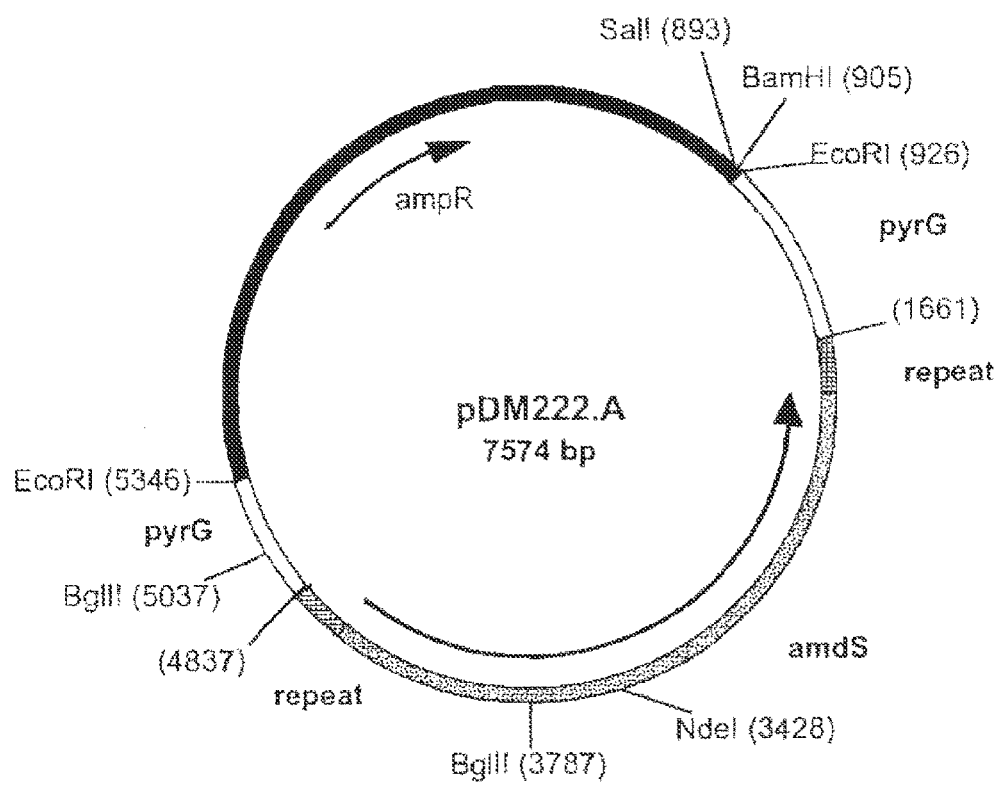
FIG. 7 shows a restriction map of pDM222A.

Plasmid pDM222A (FIG. 7) was constructed to create a 2.7 kb deletion at the pyrG locus. A 3.2 kb PmeI/SwaI *Aspergillus nidulans* amdS fragment with terminal *Aspergillus oryzae* pyrG repeats (Royer, et al., 1999, *Fungal Genetics and Biology* 28: 68-78) taken from plasmid pJRoy47.1 was cloned into pDM156.2 to replace a 2.7 kb StuI/EcoRV portion of the pyrG locus producing pDM222A. This deletion included 0.78 kb of the promoter, the entire pyrG coding region, and 0.8 kb of the terminator region. The pyrG regions flanking the amdS insert were 0.5 kb at the 5' end and 0.7 kb at the 3' end. A 4.4 kb EcoRI fragment was gel purified from the pyrG deletion plasmid pDM222A and used to transform *Fusarium venenatum* strain MLY3.

To generate spores, 10 to 15 agar plugs from a fresh *Fusarium venenatum* MLY3 strain (7-14 days) were inoculated into 500 ml of RA medium for approximately 40 hours at 26° C. with shaking at 150 rpm. Spores were harvested by filtration through sterile Miracloth (Calbiochem, La Jolla, Calif.) and spun for 20 minutes at 7974×g with Sorvall RC-5B centrifuge. The pellet was rinsed twice with 40 ml of distilled water followed by centrifugation at 1877×g for 20 minutes with Sorvall RT 6000D. A cell counting chamber (VWR Scientific, West Chester, Pa.) was used to determine the number of spores.

Protoplasts for transformation were generated as described below. A milliliter of fresh spores ($2\times10^8$/ml) was inoculated into a 500 ml baffled shake flask containing 100 ml of YP-5% glucose broth and incubated at 23.5° C. for 16 hours at 150 rpm. The culture was filtered through sterile Miracloth followed by two rinses with 50 ml of distilled water and one rinse with sterile 50 ml of 1 M $MgSO_4.7H_2O$ (0.2 µm filtered). Germlings were collected using a sterile spatula and were resuspended with 100 mg of NOVOZYME 234™ (Novozymes A/S, Bagsvaerd, Denmark) in 20 ml 1 M $MgSO_47H_2O$. After resuspension, the tube was incubated at 29° C., 90 rpm for 1 hour. Thirty milliliter of 1 M sorbitol was added to the tube followed by centrifugation for 10 minutes at 470×g. The supernatant was discarded, and the pellet was resuspended in 1 ml of 1 M sorbitol followed by addition of 30 ml of 1 M sorbitol. The tube was centrifuged at 469×g for 5 minutes. The supernatant was discarded, and the pellet was resuspended in 1 ml of 1 M sorbitol followed by addition of 30 ml of 1 M sorbitol. Before centrifugation for 5 minutes at 470×g, a 100 µl aliquot was transferred to an Eppendorf tube containing 900 µl of STC (0.8 M sorbitol, 25 mM, pH 8.0 Tris, 50 mM $CaCl_2$) to determine the number of protoplasts. The supernatant was discarded and the pellet was resuspended in STC:SPTC (40% PEG, 0.8 M sorbitol, 25 mM Tris pH 8.0, 50 mM $CaCl_2$):DMSO (9:1:0.1) to a final concentration of $5\times10^7$ protoplasts/ml. Protoplasts were stored at −80° C. until use.

For transformation the transforming DNA was mixed with 2 ml of protoplasts ($5\times10^7$/ml) in a 50 ml Falcon tube followed by 50 µl of heparin (5 mg/ml in STC) and 100 µg of DNA. The contents were gently mixed by rotation, and the tube was incubated on ice for 30 minutes. A 200 µl volume of SPTC was slowly added to the tube followed by 10 minutes of incubation at room temperature. An additional volume of 20 ml of SPTC was added to the reaction and gently mixed followed by 10 minutes of incubation at room temperature. Two ml of the transformation reaction was added to a Falcon tube containing 25 ml of COVE top agarose plus 10 mM uridine and the contents were mixed by gently inverting the tube. The mixture was then plated onto an underlay containing COVE medium.

The transformants were transferred to Vogel's acetamide agar plus or minus 10 mM uridine. Transformants which grew poorly on uridine minus medium were transferred to liquid minimal medium with and without 10 mM uridine. Mycelia were collected from strains which grew well in uridine supplemented medium but did not grow without uridine. Genomic DNA was prepared by inoculating three agar plugs from a minimal medium plate supplemented with uridine containing the fungal strain of interest into a 125 ml flask containing 25 ml of M400 medium. The flask was incubated at 26° C. for 3 days with shaking at 150 rpm. Fungal mycelia were then harvested from the culture by filtration through Miracloth followed by 2 washes with TE (per liter containing 1 M Tris-HCl pH8, 0.5 M EDTA pH 8). Mycelia were placed in a 15 ml Falcon tube and frozen in liquid nitrogen. Using a mortar and a pestle, frozen mycelia were grounded to a fine powder. The fine powder was quickly transferred into a 15 ml Falcon tube and a Qiagen DNeasy Plant kit (QIAGEN, Inc., Chatsworth, Calif.) was used to extract the genomic DNA following the manufacturer's protocol. Genomic DNA was digested with EcoRI. A Southern blot was prepared and probed with a 3.2 kb fluoroscein-labeled pyrG fragment. The pyrG fragment contained the entire coding region plus 1.3 kb of the promoter and 1.5 kb of the terminator. The Vistra fluorescence kit RPN 5751 from Amersham Life Science was used for labeling and the manufacturers instructions were followed for hybridizing and washing the blot. However, CDP-star (Roche Molecular Biochemicals) was used for signal detection and the blot was exposed to X-ray film instead of using the STORM Fluorlmager. Transformants, which yielded the predicted 4.4 kb hybridizing band characteristic of a clean double crossover event, were grown in liquid minimal medium plus 10 mM uridine for 63 hours at 28° C., 200 rpm. Spores were isolated by micromanipulation on Vogel's acetamide medium supplemented with 10 mM uridine. One spore isolate was grown in RA sporulation medium plus uridine 30 hours at 30° C., 150 rpm. Spores were separated from the mycelia by filtration through sterile Miracloth.

A 100 µl aliquot of the spore stock (9.5×10⁵ spores) was spread onto each of 5 fluoroacetamide agar plates plus 10 mM uridine. Colonies which grew on fluoroacetamide plates were transferred to both fluoroacetamide and COVE agar. Colonies that grew well on fluoroacetamide and poorly or not at all on COVE were analyzed further. Spore isolates from three of these strains were subjected to Southern blot analysis. Genomic DNA was isolated as described above, digested with EcoRI, and probed with the pyrG probe described above. Several of the spore isolates yielded a 1.4 kb hybridizing band indicating an amdS "loop-out". One spore isolate was chosen and was designated *Fusarium venenatum* strain DLM15.

Example 7

Construction of DIG-Labeled Probes for niaD, pyrG, *Fusarium oxysporum* Trypsin Gene, and *Thermomyces lanuginosus* Lipase Gene for Southern Analysis The DIG-labeled probes for niaD, pyrG, *Fusarium oxysporum* trypsin gene, and *Thermomyces lanuginosus* lipase gene were constructed using a PCR DIG Probe Synthesis Kit (Boehringer Mannheim, Indianapolis, Ind.) following the manufacturer's guidelines. The primers listed below were used to produce the DIG-labeled probes for Southern analysis.

```
Primer 3:
5'-ACAATGTTATCAATCCTCTTA-3'        (SEQ ID NO: 23)

Primer 4:
5'-TGTCCCATGTTCTCGGTGCTA-3'        (SEQ ID NO: 24)

Primer 5:
5'-GCCGACGTGACAACCACCAAAGA-3'      (SEQ ID NO: 25)

Primer 6:
5'-CCACGGGATCAGGAGCAGCATAAA-3'     (SEQ ID NO: 26)

Primer 7:
5'-GAAGCGTCGAGATGTTCCTTG-3'        (SEQ ID NO: 27)

Primer 8:
5'-GGCAGACCGATGACTTTGG-3'          (SEQ ID NO: 28)

Primer 9:
5'-GTTCTTTGTCTCTGCGTGGAC-3'        (SEQ ID NO: 29)

Primer 10:
5'-GGATATCCGGAATGTTAGGC-3'         (SEQ ID NO: 30)
```

Primer 3 and 4 were used to generate a 3.5 kb niaD fragment derived from the niaD gene of the pDM237. Primer 5 and 6 were used to produce a 719 bp pyrG fragment from pNham1. Primer 7 and 8 were used to generate a 756 bp *Fusarium oxysporum* trypsin gene fragment from pNham2. Primer 9 and 10 were used to produce an 811 bp *Thermomyces lanuginosus* lipase fragment from pNham2.

The following components were added to PCR reactions to generate DIG-labeled probes for Southern analysis: 5 µl of PCR 10× buffer, 5 µl of DIG Synthesis Mix (vial 2), 1 µl of upper primer (50 pmol/µl), 1 µl of lower primer (50 pmol/µl), 0.75 µl of Expand™ High Fidelity enzyme mix (vial 1), 1 µl of pDM237 or pNham1 or pNham2 (50-100 ng/µl), and 35.25 µl of distilled water.

PCR reactions were performed in an Eppendorf MasterCycler with the following cycling parameters and conditions as indicated by the respected DIG probe:

For the niaD probe, 1 cycle at 95° C. for 3 minutes followed by 30 cycles at 95° C. for 1 minute, 52.9° C. for 1 minute, and 72° C. for 3½ minutes followed by 1 cycle at 72° C. for 10 minutes.

For the pryG probe, 1 cycle at 95° C. for 3 minutes followed by 30 cycles at 95° C. for 1 minute, 60.1° C. for 1 minute, and 72° C. for 1 minute followed by 1 cycle at 72° C. for 10 minutes.

For the *Fusarium oxysporum* trypsin gene probe, 1 cycle at 95° C. for 3 minutes followed by 30 cycles at 95° C. for 1 minute, 54.9° C. for 1 minute, and 72° C. for 1 minute followed by 1 cycle at 72° C. for 10 minutes.

For the *Thermomyces lanuginosus* lipase probe, 1 cycle at 95° C. for 3 minutes followed by 30 cycles at 95° C. for 1 minute, 56.8° for 1 minute, and 72° C. for 1 minute followed by 1 cycle at 72° C. for 10 minutes.

PCR products were resolved on a 0.75% agarose gel in 1×TAE running buffer. The amplified DNA fragments were excised from the gel and purified using a Qiaquick Gel Extraction kit following the manufacturer's protocol.

Example 8

Construction of *Fusarium venenatum* niaD Mutant

Plasmid pNham1 (Example 3) was used to construct a *Fusarium venenatum* niaD mutant. pNham1 was linearized with XhoI and EcoRI and transformed into the *Fusarium venenatum* pyrG mutant strain DLM15 (Example 6). For the transformation, 50 μg of the linearized pNham1 was used per transformation reaction as described in Example 7. One hundred and fourteen transformants grew on Vogels $NH_4H_2PO_4$ plates, and fifty of the transformants were tested for growth on chlorate plates. Forty of the fifty transformants tested for growth on chlorate were resistant to chlorate as expected for a niaD mutant. These 40 chlorate resistance transformants were further evaluated for their ability to use nitrite rather than nitrate as the sole nitrogen source on minimal medium. All chlorate resistant transformants grew on nitrite as sole nitrogen source which is a phenotype characteristic of niaD mutants.

Six putative niaD mutant strains were selected to be analyzed and confirmed by Southern analysis. Genomic DNA was isolated from all six strains as follows. Three agar plugs were removed from a minimal medium plate containing the fungal strain of interest and placed in a 125 ml flask containing 25 ml of M400 medium. The flask was incubated at 26° C. for 3 days with shaking at 150 rpm. Fungal mycelia were then harvested from the culture by filtration through Miracloth followed by 2 washes with TE (per liter containing 1 M Tris-HCl pH8, 0.5 M EDTA pH 8). Mycelia were placed in a 15 ml Falcon tube and frozen in liquid nitrogen. Using a mortar and a pestle, frozen mycelia were grounded to a fine powder. The fine powder was quickly transferred into a 15 ml Falcon tube and a Qiagen DNeasy Plant kit (QIAGEN, Inc., Chatsworth, Calif.) was used to extract the genomic DNA following the manufacturer's protocol.

For Southern analysis, genomic DNA from the six putative niaD disrupted strains were digested with PstI, NsiI, and EcoRV and probed with either the 3.6 Kb niaD fragment from pDM237 (Example 8) or with the 780 bp pyrG fragment (Example 8) from pNham1. Genomic DNA from niaD mutants and untransformed DLM15 strain were digested with Nsi I and Pst I, EcoRV, and BamHI overnight at 37° C. (11 μl of distilled water, 5 μl of genomic DNA (3 μg), 2 μl of 10× buffer, and 2 μl of the restriction endonucleases). After digestion, each reaction was resolved on a 1% agarose gel using TAE buffer containing 2 μl of ethidium bromide. The gels were submerged in 250 mM HCl for 10 minutes at room temperature with gentle agitation. The gels were rinsed in water for 5 minutes and then placed into denaturation buffer (0.5 M NaOH, 1.5 M NaCl) and gently agitated twice for 15 minutes at room temperature followed by a 5 minute rinse with water. The gels were then submerged in neutralization buffer (1 M Tris pH 8, 1.5 M NaCl) and gently agitated twice for 15 minutes at room temperature. The DNA was transferred to a Hybond™ membrane using Schleicher & Schuell Turblotter (Schleicher & Schuell Inc. Keene, N.H.) with 10×SSC (1.5 M NaCl and 1.5 M sodium citrate) overnight.

On day two, the membranes were gently rinsed with 2×SSC for 5 minutes and then crosslinked in an UV Stratalinker™ (Stratagene, La Jolla, Calif.) at 120,000 joules/$cm^2$. The dried blots were then pre-hybridized in a glass tube containing 30 ml of DIG Easy Hyb at 42° C. for at least 2 hours. After that time, the prehybridization solution was discarded and replaced with 7.5 ml of fresh DIG Easy Hyb containing 40 μl of gel purified DIG-labeled probe generated by PCR, which had been denatured in a boiling water bath for 10 minutes. The hybridization tube was incubated at 42° C. in a Hybaid (National Labnet Company Woodbridge, N.J.) oven overnight.

After hybridization, each blot was washed twice for 5 minutes in 300 ml of 2×SCC, 0.1% SDS solution at room temperature with gentle rotation in the same hybridization tube and two more washes for 15 minutes in 300 ml of 0.2×SSC, 0.1% SDS solution at 65° C. Each blot was then equilibrated in 150 ml of 1× wash buffer (15 ml 10× wash buffer [Roche Mannheim, Germany] and 135 ml distilled $H_2O$) with gentle agitation at room temperature for 1 minute. The wash buffer was discarded and 100 ml of 1× block solution (10 ml 10× block [Roche Mannheim, Germany], 10 ml 10× maleic acid [Roche Mannheim, Germany], and 80 ml of distilled water) was added to each blot followed by gentle agitation at room temperature for at least 60 minutes. The block solution was discarded and each blot was incubated in 30 ml of anti-digoxigenin-AP solution (diluted 1:20,000 in 1× blocking solution) with gentle agitation for 15 minutes. Each blot was washed twice in 130 ml of 1× wash buffer for 20 minutes with gentle agitation at room temperature. The blots were then equilibrated for 5 minutes each in 40 ml of 1× detection buffer (4 ml of 10× detection (Roche) and 36 ml of distilled water) with gentle agitation at room temperature. Each blot was placed on an acetate sheet and 1 ml of chemiluminescent substrate (CDP-Star™ diluted 1:100 in 1× detection buffer) was applied onto each blot. The blots were covered with a second acetate sheet and incubated for 5 minutes at room temperature. The blots were exposed to X-ray films in a metal cassette for 10-15 minutes or until desired exposure was obtained.

Southern analysis demonstrated that three of the six transformants had the expected gene replacement at the niaD locus. The three transformants contained the pyrG gene, which was integrated by a double crossover event to disrupt the niaD gene. PstI digested genomic DNA from niaD transformants produced 869 bp and 1.6 kb bands as well as a third band of >8.5 kb. The untransformed *Fusarium venenatum* strain DLM15 produced a 3.3 kb band and a >8.5 kb band when probed with the niaD fragment. NsiI digested genomic DNA produced a 687 bp and a 1.7 kb band as well as a third band of >8.5 kb. The untransformed *Fusarium venenatum* strain DLM15 produced a 680 bp and a >8.5 band when probed with the identical niaD fragment. In addition, the three niaD transformants were digested with EcoRV, which produced a 4.5 kb and a 1.9 kb band when probed either with a niaD fragment or a pyrG fragment. EcoRV digested DNA of the untransformed *Fusarium venenatum* strain DLM15 produced three bands of 1.2 kb, 1.5 kb, and 4.2 kb when probed with the niaD fragment and no bands were observed when probed with the pyrG fragment.

The following procedure for spore purification was performed twice in order to obtain a purified fungal strain. Three agar plugs were removed from a minimal medium plate containing the fungal strain and placed in a 125 ml flask containing 25 ml of RA medium. The flask was incubated at 26° C. for 40 hours with shaking at 150 rpm. Fungal spores were then harvested from the culture by filtration through Miracloth and centrifuged for 10 minutes at 1877×g with Sorvall RT 6000D centrifuge. The pellet was rinsed twice with 40 ml of distilled water followed by centrifugation at 1877×g for 20 minutes. Appropriate dilutions of the spores were plated on minimal medium plates to obtain isolated colonies. Individual colonies were transferred to minimal medium plates and grew for 5-7 day and subsequent spore purification process was repeated.

*Fusarium venenatum* niaD mutant #3 was selected according to protoplast and lipase yields obtained for all three transformants: niaD mutant #3 produced slightly higher observed lipase yield when compared to niaD mutant #2 and niaD mutant #3 rendered a higher number of protoplasts when compared to niaD mutant #4. Hence, niaD mutant #3 was the selected strain used as the host for the analysis of pNham2 and pNham2 variants.

Example 10

Construction of pNham2 Promoter Variants

Thirteen promoter variants of pNham2 were produced by deletion, substitution, and insertion of nucleotide sequences using the Stratagene QuikChange™ Site-Directed Mutagenesis Kit (Stratagene Cloning System, La Jolla, Calif.) following the manufacturer's guidelines and using the primers listed below:

```
Primer 15:
                                           (SEQ ID NO: 31)
5'-CACGAACGCCTGCTCTATAGCGCCAATGAGG-3'

Primer 16:
                                           (SEQ ID NO: 32)
5'-CCTCATTGGCGCTATAGAGCAGGCGTTCGTG-3'

Primer 17:
                                           (SEQ ID NO: 33)
5'-CGACCAGACTAAACCATGCGGGGATTGGGG-3'

Primer 18:
                                           (SEQ ID NO: 34)
5'-CCCCAATCCCCCGCATGGTTTAGTCTGGTCG-3'

Primer 19:
                                           (SEQ ID NO: 35)
5'-GGCGTAATTTATACCATAGCGGGAAACTCCTGTTTTGTCAAG-3'

Primer 20:
                                           (SEQ ID NO: 36)
5-CTTGACAAAACAGGAGTTTCCCGCTATGGTATAAATTACGCC-3'

Primer 21:
                                           (SEQ ID NO: 37)
5'-CGAACGCCTGCTCTCGTAATTTATACC-3'

Primer 22:
                                           (SEQ ID NO: 38)
5'-GGTATAAATTACGAGAGCAGGCGTTCG-3'

Primer 23:
                                           (SEQ ID NO: 39)
5'-CTCGGCGTAATTTCGGCCATAGCGCCAATG-3'

Primer 24:
                                           (SEQ ID NO: 40)
5'-CATTGGCGCTATGGCCGAAATTACGCCGAG-3'

Primer 25:
                                           (SEQ ID NO: 41)
5'-CGCCTGCTCTCGGAAATTTAAATACCATAGCGCC-3'

Primer 26:
                                           (SEQ ID NO: 42)
5'-GGCGCTATGGTATTTAAATTTCCGAGAGCAGGCG-3'

Primer 27:
                                           (SEQ ID NO: 43)
5'-CGCCTGCTCTCGGAAATTTAACGGCCATAGCGCCAATG-3'

Primer 28:
                                           (SEQ ID NO: 44)
5'-CATTGGCGCTATGGCCGTTAAATTTCCGAGAGCAGGCG-3'

Primer 29:
                                           (SEQ ID NO: 45)
5'-GCCTGCTCTCGGAAATTTAAAAATTTAACGGCCATAGCGCCAATG-3'

Primer 30:
                                           (SEQ ID NO: 46)
5'-ATTGGCGCTATGGCCGTTAAATTTTAAATTTCCGAGAGCAGGCG-3'

Primer 31:
                                           (SEQ ID NO: 47)
5'-CGAACGCCTGCTCTTATATGCCGGGCGCAAATAGCGCCAATGAG-3'

Primer 32:
                                           (SEQ ID NO: 48)
5'-CTCATTGGCGCTATTTGCGCCCGGCATATAAGAGCAGGCGTTCG-3'

Primer 33:
                                           (SEQ ID NO: 49)
5'-CGAACGCCTGCTCTATTCGTAATTTATACC-3'

Primer 34:
                                           (SEQ ID NO: 50)
5'-GGTATAAATTACGAATAGAGCAGGCGTTCG-3'

Primer 35:
                                           (SEQ ID NO: 51)
5'-CGTAATTTATACCATAGCGAAGGGTCTTTAGGAAACTCCTGTTTTGTC-3'

Primer 36:
                                           (SEQ ID NO: 52)
5'-GACAAAACAGGAGTTTCCTAAAGACCCTTCGCTATGGTATAAATTACG-3'

Primer 37:
                                           (SEQ ID NO: 53)
5'-CTCCTGTTTTGTCGGCGTAATTTCGGCCGTTGGGTCATG-3'

Primer 38:
                                           (SEQ ID NO: 54)
5'-CATGACCCAACGGCCGAAATTACGCCGACAAAACAGGAG-3'
```

Primers 15 and 16 were used to create pNham2-Del.1, which contained a deletion spanning the nucleotide sequence of CGGCGTAATTTATACC at positions −158 to −143 upstream of the *Fusarium venenatum* glucoamylase promoter which corresponded to nucleotides 1952 to 1967 of SEQ ID NO: 1 (SEQ ID NO: 68).

Primers 17 and 18 were used to create pNham2-Del.2, which contained a deletion spanning the nucleotide sequence of CGGGAGAGTGTCAAAT at positions −272 to −257 upstream of the *Fusarium venenatum* glucoamylase promoter which corresponded to nucleotides 1838 to 1853 of SEQ ID NO: 1 (SEQ ID NO: 2).

Primers 19 and 20 were used to create pNham2-Del.3, which contained a deletion spanning the nucleotide sequence of CCAATGAGGGC at positions −134 to −124 upstream of the *Fusarium venenatum* glucoamylase promoter which corresponded to nucleotides 1974 to 1984 of SEQ ID NO: 1 (SEQ ID NO: 6).

Primers 21 and 22 were used to create pNham2-Del.4, which contained a deletion spanning the CGG nucleotides of the sequence of CGGCGTAATTTATACC at positions −158 to −156 upstream of the *Fusarium venenatum* glucoamylase promoter which corresponded to nucleotides 1952 to 1954 of SEQ ID NO: 1 (SEQ ID NO: 7).

Primers 23 and 24 were used to create pNham2-Sub.1, which contained a substitution of ATA with a CGG triplet located at positions −147 to −145 upstream of the *Fusarium venenatum* glucoamylase promoter which corresponded to nucleotides 1963 to 1965 of SEQ ID NO: 1. This substitution produced a promoter variant comprising the sequence of CGGCGTAATTTCGGCC (SEQ ID NO: 3).

Primers 25 and 26 were used to create pNham2-Sub.2, which contained the consensus of AAATTTAA within the sequence of CGGCGTAATTTATACC. This substitution produced a promoter variant containing the sequence of CGGAAATTTAAATACC at positions −155 to −148 of the *Fusarium venenatum* glucoamylase promoter which corresponded to nucleotides 1955 to 1962 of SEQ ID NO: 1 (SEQ ID NO: 8).

Primers 27 and 28 were used to create pNham2-Sub.3, which contained the sequence CGGAAATTTAACGGCC substituted at positions −155 through −145 from the start codon. This substitution corresponds to nucleotides 1955 to 1965 of SEQ ID NO: 1 (SEQ ID NO: 9).

Primers 29 and 30 were used to create pNham2-Ins.1, which contained an insertion of the consensus of AAATTTAA within pNham2-Sub.3 variant located between −148 to −147 which corresponded to nucleotides 1962 to 1963 of SEQ ID NO: 1 (SEQ ID NO:10). This insertion produced a variant comprising the sequence of CGGAAATTTAAAAATTTAACGG.

Primers 31 and 32 were used to create pNham2-Sub.4, which contained the substituted sequence of TATATGCCGGGCGCAA located at positions −158 to −143 of the *Fusarium venenatum* glucoamylase promoter which corresponded to nucleotides 1952 to 1967 of SEQ ID NO: 1 (SEQ ID NO: 69).

Primers 33 and 34 were used to create pNham2-Sub.5, which contained the sequence ATT substituted for CGG at positions −158 to −156 of the *Fusarium* venenatum glucoamylase promoter which corresponded to nucleotides 1952 to 1954 of SEQ ID NO: 1 (SEQ ID NO: 11). This substitution produced a variant comprising the sequence of ATTCGTAATTTATACC.

Primers 35 and 36 were used to create pNham2-Sub.6, which contained the substituted sequence of AAGGGTCTTTA located at positions −134 to −124 of the *Fusarium* venenatum glucoamylase promoter which corresponded to nucleotides 1974 to 1984 of SEQ ID NO: 1 (SEQ ID NO: 12).

pNham2-Sub.7 was created using pNham2-Del.2 with primer 23 and 24 to substitute ATA with a CGG triplet located at positions −147 to −145 upstream of the *Fusarium* venenatum glucoamylase promoter which corresponded to nucleotides 1963 to 1965 of SEQ ID NO: 1 (SEQ ID NO: 4).

Primers 37 and 38 were used to create pNham2-Sub.8 (from pNham2-Sub.1) which contained an additional copy of the sequence CGGCGTAATTTCGGCC (SEQ ID NO: 70) substituted at positions −108 through −93 of the *Fusarium venenatum* glucoamylase promoter which corresponded to nucleotides 2002 to 2017 of SEQ ID NO: 1 (SEQ ID NO: 5).

All pNham2 *Fusarium venenatum* glucoamylase promoter variants generated by site-directed mutagenesis were confirmed by sequencing. Sequence analyses were performed on the *Fusarium venenatum* glucoamylase promoter, the *Thermomyces lanuginosus* lipase gene, and part of the *Fusarium oxysporum* trypsin terminator in the pNham2 variants. The following primers were used to confirm the sequence of the variants:

```
Primer 39.
5'-CGAACAGACGCCTCCGAAGAG-3'    (SEQ ID NO: 55)

Primer 40.
5'-GTGACATCGCCCACTCCAGAG-3'    (SEQ ID NO: 56)

Primer 41.
5'-GATGTTACGACGTGGGCCTGA-3'    (SEQ ID NO: 57)

Primer 42.
5'-ACGCCGCAGCCGAGAC-3'         (SEQ ID NO: 58)
```

-continued

```
Primer 43.
5'-CTGGTTATTGCCGCCG-3'         (SEQ ID NO: 59)

Primer 44.
5'-TACCGCATTACCCACACCAAT-3'    (SEQ ID NO: 60)

Primer 45.
5'-TGTTCGGCAGACAGATAACTG-3'    (SEQ ID NO: 61)

Primer 46.
5'-GCCCAAGACGACAGAGACGAC-3'    (SEQ ID NO: 62)

Primer 47.
5'-ATGACCTCAACATCTACCCGG-3'    (SEQ ID NO: 63)
```

Example 11

Analysis of *Fusarium venenatum* Glucoamylase Promoter Variants

The *Fusarium venenatum* niaD mutant was transformed with the wild-type pNham2 and its variants described in Example 10 to evaluate the differences in lipase yields obtained when a single copy of the construct is integrated at the niaD locus. The procedure for transformation described in Example 7 was followed and 100 µg of DNA for each variant was used per reaction followed by selection on minimal plates with a nitrite source. Transformants were selected on minimal medium plates containing nitrite as the sole source of nitrogen. Only those transformants which contain a functional niaD gene were able to grow due to integration of the expression plasmid.

Southern analysis was performed on several transformants of pNham2 or glucoamylase promoter variants thereof to determine the copy number integrated at the niaD locus as described in Example 8. Genomic DNA of several transformants for each variant was isolated as described in Example 8 and was digested with NheI and MunI. Functional niaD transformants containing a single copy of the pNham2 integrated at the niaD locus produced 4.5 kb and 9.5 kb bands when probed with the trypsin gene fragment described in Example 7. Transformants with multiple copies of the plasmid produced 4.5 kb and 9.5 kb bands as well as a third band of 11.5 kb which corresponds to the size of pNham2. The untransformed niaD mutant strain does not contain any bands when probed with the *Fusarium oxysporum* trypsin gene fragment. In addition, the Southern blots were probed with a lipase fragment (Example 7). Single integrants of pNham2 should contain only a 9.5 kb band when probed with the lipase fragment probe. Multiple integrants should contain the 9.5 kb band as well as a second band of 11.5 kb. The untransformed niaD strain did not produce any bands when probed with the lipase fragment.

Functional niaD transformants containing a single copy of the pNham2 or variants were spore purified (as described in Example 9) twice before lipase yields were assessed. A minimum of five transformants for each variant with a single copy of plasmid integrated was selected for comparison of lipase activity. Each transformant was grown in 3 separate shake flasks and assayed in triplicate for lipase activity. A 25 ml volume of M400 medium in a 125 ml flask was inoculated with 2 or 4 plugs derived from a 5-7 day plate. All flasks were incubated for 7 days at 28° C. with shaking at 200 rpm. On day 4 and 7, a 1.5 ml sample of each culture was taken and spun at 13,720×g for 30 minutes with Sorvall MC 12V table centrifuge. Supernatants were transferred into a centrifuge tube and stored at −20° C. until the lipase assay was performed.

The lipase activity was performed using the following method. The substrate used in the analysis was p-nitrophenyl butyrate (4 ml of 990 µl of DMSO, 0.1 M MOPS, and 10 µl of p-nitrophenyl butyrate). A volume of 100 µl of substrate was added to 100 µl of enzyme (diluted in 0.1 M MOPS pH 7.5, 4 µM CaCl$_2$) in a 96 well microtiter plates. Lipase activity was determined by using a standard curve generated using LIPO-LASE™ (*Thermomyces lanuginosus* lipase, Novozymes, A/S, Bagsvaerd, Denmark) at 0.1, 0.2 0.4, 0.6, 0.8. 0.9, and 1 LU/ml. Using a microplate reader, lipase activity was measured at 405 nm for 5 minutes at 25° C.

The relative lipase activity obtained for wild-type pNham2 and its promoter variants are shown in Table 1. For each variant the relative mean of lipase activity is shown as well as the p value from a t-test to determine the probability that the lipase yields for a given variant were the same as those for the wild type pNham2. The lower the p value the higher the probability that the populations are different.

TABLE 1

Lipase activity by *Fusarium venenatum* functional niaD transformants

| Strain | # Transformants Screened | Relative Mean lipase activity (LU/ml) | Prob > [t] |
|---|---|---|---|
| pNham2 | 5 | 1.0 | — |
| pNham2-Del.1 | 7 | 0.87 | 0.127 |
| pNham2-Del.2 | 9 | 1.41 | 0.0005 |
| pNham2-Del.3 | 7 | 0.34 | 0.0002 |
| pNham2-Del.4 | 7 | 0.64 | 0.0059 |
| pNham2-Sub.1 | 6 | 3.01 | 1.2E−05 |
| pNham2-Sub.2 | 7 | 0.62 | 0.0022 |
| pNham2-Sub.3 | 6 | 0.75 | 0.0140 |
| pNham2-Ins.1 | 7 | 0.51 | 0.0004 |
| pNham2-Sub.4 | 7 | 1.01 | 0.9210 |
| pNham2-Sub.5 | 6 | 0.40 | 0.0002 |
| pNham2-Sub.6 | 5 | 0.25 | 7.5E−05 |
| pNham2-Sub.7 | 8 | 2.72 | 9.9E−06 |
| pNham2-Sub.8 | 5 | 6.04 | 1.8E−10 |

Plasmid pNham2-Del.1 contained the deleted putative region IIIa showed no significant change in lipase activity as compared to the wild type plasmid pNham2. pNham2-Del.2 showed a slight increase in lipase activity. Both pNham2-Del.3 and pNham2-Del.4 showed significant decrease in lipase activity as compared to the wild-type.

pNham2-Sub.1 showed a significant increase in lipase activity by approximately 3-fold when a CGG triplet is substituted at positions −147 to −145 of the *Fusarium venenatum* glucoamylase promoter.

pNham2-Sub.(2-3) and pNham2-Ins.4 showed significant reduction in lipase activity.

Substitution analyses of pNham2 Sub.4-6 variants were performed to determine whether the lipase yields obtained with pNham2-Del.1, 3, and 4 were due to position effects or the deletion of important promoter elements. There was no significant difference in lipase activity when comparing pNham2-Sub.4 to pNham2-Del.1 and wild-type pNham2. Hence, pNham2-Sub.4 substantiates that the result of pNham2-Del.1 variant was not caused by position effect. The findings of pNham2-Sub.5 and 6 substantiate the results of pNham2-Del. 3 and 4. Thus, it suggested that the deleted nucleotides are promoter elements, which may be responsible for high-level expression of the glucoamylase promoter.

pNham2-Sub.7 variant was created to test for an additive effect in expression level. pNham2-Sub.7 variant was constructed by combining the mutations in pNham2-Del.2 and pNham2-Sub.1. There was no additive effect shown by pNham2-Sub.7 in terms of lipase activity. In fact, there was no significant change in expression observed between pNham2-Sub.7 and pNham2-Sub.1.

With pNham2-Sub.8, which contained an additional CGGCGTAATTTCGGCC (SEQ ID NO: 70) at positions −108 to −93 of the glucoamylase promoter, a six fold increase in lipase yield was observed in comparison to pNHam2. This finding suggests that the improvement of the glucoamylase promoter activity can be achieved by the introduction of multiple copies of CGGCGTAATTTCGGCC (SEQ ID NO: 70) upstream of the start codon.

Example 12

Construction of a DIG-Labeled Histone/Lipase Hybrid Probe for Northern Analysis

A histone/lipase hybrid probe was produced using the following set of primers:

```
Primer 11:
                                        (SEQ ID NO: 64)
5'-TCTGGAGTGGGCGATGTCA-3'

Primer 12:
                                        (SEQ ID NO: 65)
5'-ACCAGTGGACTTGCGGGCGTACCCATTTCCACGCAGGTC-3'

Primer 13:
                                        (SEQ ID NO: 66)
5'-GACCTGCGTGGAAATGGGTACGCCCGCAAGTCCACTGGT-3'

Primer 14:
                                        (SEQ ID NO: 67)
5'-GGATGGCGCAGAGGTTGGTG-3'
```

Primers 11 and 12 were used to generate a 320 bp histone fragment derived from a cDNA H3 histone fragment (WO 2000/56762). Primers 13 and 14 were used to produce a 320 bp lipase fragment from pNham2. Primers 11 and 14 were used to generate a 620 bp histone/lipase fragment from the PCR products of the histone and lipase reactions.

PCR components used for generating the histone and lipase fragment were as follows: Histone or lipase fragment: 1 µl of DNA (histone cDNA or pNham2) approx. 50 ng, 5 µl of 10× Taq buffer (Roche), 1 µl of 25 mM dNTPs (Boehringer Mannheim, Indianapolis, Ind.), 1 µl of 50 pmol primer 11 or 12, 1 µl of 50 pmol primer 13 or 14, 1 µl of 5 units/µl Taq polymerase (Roche), and 40 µl of distilled water. The cycling parameters and conditions for PCR were as follows: Histone or Lipase fragments: 1 cycle at 95° C. for 3 minutes followed by 25 cycles at 95° C. for 30 seconds, 60° C. for 30 seconds, and 72° C. for 1 minute followed by 1 cycle at 72° C. for 10 minutes.

The PCR Dig Probe Synthesis Kit was used to generate the histone/lipase hybrid probe with the following components: 5 µl of PCR 10× buffer, 5 µl of Dig Synthesis Mix, 1 µl of primer 11 (50 pmol/µl), 1 µl of primer 14 (50 pmol/µl), 1 µl of Expand™ High Fidelity enzyme mix, 1 µl of the histone PCR product, 1 µl of the lipase PCR product, and 35 µl of distilled water.

The PCR reaction was performed in an Eppendorf Master-Cycler with the following cycling parameters and conditions: 1 cycle at 95° C. for 3 minutes followed by 30 cycles at 95° C. for 1 minute, 60° C. for 1 minute, and 72° C. for 1 minute followed by 1 cycle at 72° C. for 10 minutes. The 640 bp PCR product was resolved on a 0.75% agarose gel using TAE running buffer, excised from the gel, and purified using a Qiaquick Gel Extraction kit following the manufacturer's protocol.

Example 13

Northern Analysis of Transformants Containing a Single Copy of the pNham2 Variant Constructs Northern analysis was performed on a number of pNham2 promoter variants to determine if the differences in lipase yields observed between the transformants were due to differences in the amount of lipase mRNA transcripts present in the cell. Two transformants were chosen for each of six pNham2 variants.

Three agar plugs were removed from a minimal medium plate containing the fungal strain of interest and placed in a 125 ml flask containing 25 ml of M400 medium. The flask was incubated at 28° C. for 3 days with shaking at 200 rpm. Fungal mycelia were then removed from the culture and used for RNA extraction. The Bio 101 FastRNA Kit RED (Qbiogene, Inc., Carlsbad, Calif.) was used to extract RNA from the mycelia following the manufacturer's protocol.

Ten micrograms of total RNA from each transformant were aliquoted into a microcentrifuge tube and the content was dried by speed vacuum with medium heat until the volume was approximately 5 µl. A 15 µl volume of NorthernMAX™ Gel Loading Solution (AMBION, Austin, Tex.) was added to each sample and vortexed to resuspend. Samples were heated in boiling water for 2 minutes, then quickly spun in a microfuge and chilled on ice.

Samples were loaded onto a 1.5% formaldehyde agarose gel in MOPS buffer (Amersco Solon, Ohio), and the gel was run at 100 volts until the bromophenol blue dye migrated approximately three-fourths down the gel length. The formaldehyde gel was prepared by mixing 1.5 g agarose, 10 ml 10×MOPS buffer and 85 ml $H_2O$ in a beaker. The agarose was dissolved by heating and then cooling to 50° C. with an addition of 5 µl of EtBr and 5.4 ml 37% formaldehyde. The gel was rinsed with DEPC-treated water to remove formaldehyde, then transferred to a HyBond N+ membrane overnight at 4° C. using a Schleicher & Schuell Turboblotter (Schleicher & Schuell, Keene, N.H.) and 10×SSC buffer.

Following transfer, the membrane was dried in a vacuum oven at 80° C. for 10 minutes. The membrane was scanned using a STORM 860 Phosphoimager (Molecular Dynamics Piscataway, N.J.) with blue fluorescent mode at 1000 PMT voltage to image the RNA on the membrane for subsequent quantitation. Then, the membrane was rinsed twice with 2×SSC buffer for 5 minutes with gentle agitation and crosslinked in a UV Stratalinker (Stratagene, La Jolla, Calif.).

The prehybridization and hybridization procedures for Northern analysis were performed as previously described for Southern analysis (Example 8). However, the blot was equilibrated in Buffer A (0.3 M NaCl, 0.1 M Tris-HCl, at pH 7.5) prior to detection. Following detection, the membrane was exposed to ECF substrate (Amersham Pharmacia Biotech., Buckinghamshire, England) overnight. The quantification of both histone and lipase mRNA levels was determined by using the STORM 860 Phosphoimager and Image Quant (version 5.0) program. The results obtained are shown in Table 2.

TABLE 2

Northern analysis of pNham2 variants

| Strain | Mean Ratio of lipase to histone mRNA level | Mean relative lipase activity (LU/ml) |
|---|---|---|
| pNham2 | 0.22 | 1.0 |
| pNham2-Del.1 | 0.23 | 0.87 |
| pNham2-Del.2 | 0.33 | 1.41 |
| pNham2-Del.3 | 0.14 | 0.34 |
| pNham2-Del.4 | 0.19 | 0.64 |
| pNham2-Sub.1 | 0.63 | 3.01 |
| pNham2-Sub.2 | 0.18 | 0.62 |
| pNham2-Sub.5 | 0.12 | 0.40 |
| pNham2-sub.8 | 1.19 | 6.04 |

Table 2 shows there was no difference in the lipase to histone mRNA ratio between wild-type and pNham2-Del. 1 which was consistent with the relatively equivalent lipase yields observed. In contrast, there were significant differences between other pNham2 variants when compared to the wild-type pNham2. The increased lipase mRNA transcript level in pNham2-Del.2 and pNham2-Sub.1 correlated well with the increased lipase yields observed when compared to pNham2. This correlation suggested that transcriptional efficiency of the glucoamylase promoter accounted for the increase in lipase yields. The reduction of lipase mRNA levels observed in pNham2-Del.3-Del.4 and pNham2-Sub.2 correlated well with the decreased lipase yields. These findings indicated that transcriptional control accounts for the reduced lipase yield due to the deletion of the CGG and CCAATGAGGGC, and the addition of AAATTTAA consensus sequence did not lead to an increase in expression.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| E. coli TOP10 (pECO3) | NRRL B-30067 | Oct. 27, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents substantially pure culture of the deposited strain. The deposit is as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide, comprising:
   (a) cultivating a fungal host cell in a medium conducive for the production of the polypeptide, wherein the fungal host cell comprises a first nucleic acid sequence encoding the polypeptide operably linked to a second nucleic acid sequence comprising a tandem promoter comprising at least SEQ ID NO: 2; and
   (b) isolating the polypeptide from the cultivation medium.

2. The method of claim 1, wherein the fungal host cell contains one or more copies of the first nucleic acid sequence.

3. The method of claim 1, wherein the fungal host cell contains one copy of the first nucleic acid sequence.

4. The method of claim 1, wherein the polypeptide is selected from the group consisting of an antigen, enzyme, growth factor, hormone, immunodilator, neurotransmitter, receptor, reporter protein, structural protein, and transcription factor.

5. The method of claim 1, wherein the polypeptide is native or foreign to the fungal host cell.

6. The method of claim 1, wherein the tandem promoter comprises SEQ ID NO: 2 and one or more promoters selected from the group consisting of SEQ ID NO: 3, SEQ ID NO: 4, and SEQ ID NO: 5.

7. The method of claim 1, wherein the tandem promoter comprises at least two copies of SEQ ID NO: 2.

8. An isolated tandem promoter comprising at least SEQ ID NO: 2.

9. The tandem promoter of claim 8, wherein the tandem promoter comprises SEQ ID NO: 2 and one or more promoters selected from the group consisting of SEQ ID NO: 3, SEQ ID NO: 4, and SEQ ID NO: 5.

10. The tandem promoter of claim 8, wherein the tandem promoter comprises at least two copies of SEQ ID NO: 2.

11. A nucleic acid construct comprising a nucleic acid sequence encoding a polypeptide operably linked to the promoter variant of claim 8.

12. A recombinant expression vector comprising the nucleic acid construct of claim 11.

13. A recombinant host cell comprising the nucleic acid construct of claim 11.

14. A method for producing a polypeptide, comprising (a) cultivating a homologously recombinant cell, having incorporated therein an introduced transcription unit comprising the tandem promoter of claim 8, an exon, and/or a splice donor site operably linked to a second exon of an endogenous nucleic acid sequence encoding the polypeptide, under conditions conducive for production of the polypeptide; and (b) recovering the polypeptide.

\* \* \* \* \*

```
                         SEQUENCE LISTING

<160> NUMBER OF SEQ ID NOS: 69

<210> SEQ ID NO 1
<211> LENGTH: 2112
<212> TYPE: DNA
<213> ORGANISM: Fusarium venenatum

<400> SEQUENCE: 1
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg     180
aatgacaaac ctacgggtcc gttcttgaga agtggcctga gatttctcac ttggtgagaa     240
aaaggacggg cgagcgggag cctgagtcag aagaaatacc tgtctccttg gatctcacat     300
gacggtgttg tggaagagtg catctattgt cattgctgga gtgacggcag agtaggggtc     360
taaagaaacc catactgagt agagatggag aagacaacaa aagcccaaga cgacagagac     420
gacagaagat taaagctatc agagcgagac tatatcacta ttcgaaacct gcgagtaatt     480
taacaagaag tacacatcat cattgttatc aattcgacga agacatggtc gaaaattctt     540
gcggtgtata tgtctgttgt atatgggcct gggcattgtt attttcgcc gtctttatgt      600 gtactaacac ttccattgat accccagaac aaaagatgaa cgcttaaaca gcaccaaaat     660
caggagaaga atggcgctgc tctaggtatg cttctgggat aaaaagcgat gttgatacct     720
ctcagaaaag aagtgatttg aagttgaatc aaacaaatag ccgatggagc gatctgaagg     780
ggtggcagac ctgctacgcg catttaggca aggcatcaac tcggcagatg attaagaaag     840
gttttgtagg ttcacgtgtt gtgttgtgtt ccattataag tttataacct tgctaagatg     900
caacgactct gacctcaggg tgttagaaaa attgaccact aggagcataa gtgacgaaat     960
tcggggatca agacaataga tagtttcatt ttcatgtgct cctacgtctt ttcacgtaat    1020
gtttcttata aaaaaaaga tagcattgtc tctttggtga aaagagaaaa aaagatgtta    1080
cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt ctttttttta atcaacagaa    1380
acgttccatg ttcatttgtt aatccaatct atttgtgata gcgtttgatg acaaacaata    1440
ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacggcca    1740
actaacgtcc aaaaggcccg aaaaacgtcc atcacgccgc agccgagact tcaatagact    1800
gcacaagaag gaccgatgag atcgaccaga ctaaacccgg gagagtgtca aatatgcggg    1860
ggattgggga acttaccccca gaaaagagaa ggaggataaa ttccatgtct ggggttgacg    1920
tctctattgg ttagacacga acgcctgctc tcggcgtaat ttataccata gcgccaatga    1980
```

```
gggcggaaac tcctgttttg tcaagtcgtc attgttggtt gggtcatgat atatagccag   2040
taggtatccg tcttggtgat tgaccagaca tatcgctcat cacagatcaa catcactgct   2100
atcaccaaca tg                                                       2112

<210> SEQ ID NO 2
<211> LENGTH: 2096
<212> TYPE: DNA
<213> ORGANISM: Fusarium venenatum

<400> SEQUENCE: 2
cctcacccat ctcaacacct gtcgtgtgct cacttgacta cttctttgaa ccagctcgcc     60
atcggactag tcgaacaagc ttgtcgcccc catacagatg aatgtatgtt taaagctaca    120
tgatcagcct gaaccgagca taactcgagt gccgagactc ctctgatgta tatcgagatg    180
aatgacaaac ctacgggtcc gttcttgaga agtggcctga gatttctcac ttggtgagaa    240
aaaggacggg cgagcgggag cctgagtcag aagaaatacc tgtctccttg gatctcacat    300
gacggtgttg tggaagagtg catctattgt cattgctgga gtgacggcag agtaggggtc    360
taaagaaacc catactgagt agagatggag aagacaacaa agcccaaga cgacagagac     420 gacagaagat taaagctatc agagcgagac tatatcacta ttcgaaacct gcgagtaatt    480
taacaagaag tacacatcat cattgttatc aattcgacga agacatggtc gaaaattctt    540
gcggtgtata tgtctgttgt atatgggcct ggcattgtt attttcgcc gtctttatgt      600 gtactaacac ttccattgat accccagaac aaagatgaa cgcttaaaca gcaccaaaat    660
caggagaaga atggcgctgc tctaggtatg cttctgggat aaaaagcgat gttgatacct    720
ctcagaaaag aagtgatttg aagttgaatc aaacaaatag ccgatggagc gatctgaagg    780
ggtggcagac ctgctacgcg catttaggca aggcatcaac tcggcagatg attaagaaag    840
gttttgtagg ttcacgtgtt gtgttgtgtt ccattataag tttataaccct tgctaagatg    900 caacgactct gacctcaggg tgttagaaaa attgaccact aggagcataa gtgacgaaat    960
tcggggatca agacaataga tagtttcatt tcatgtgct cctacgtctt ttcacgtaat    1020
gtttcttata aaaaaaaga tagcattgtc tctttggtga aagagaaaa aaagatgtta     1080 cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt cttttttta atcaacagaa     1380 acgttccatg ttcatttgtt aatccaatct atttgtgata gcgtttgatg acaaacaata    1440
ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacggcca    1740
actaacgtcc aaaaggcccg aaaaacgtcc atcacgccgc agccgagact tcaatagact    1800
gcacaagaag gaccgatgag atcgaccaga ctaaaccatg cggggggattg gggaacttac    1860 cccagaaaag agaaggagga taaattccat gtctggggtt gacgtctcta ttggttagac    1920
acgaacgcct gctctcggcg taatttatac catagcgcca atgagggcgg aaactcctgt    1980
```

```
tttgtcaagt cgtcattgtt ggttgggtca tgatatatag ccagtaggta tccgtcttgg    2040
tgattgacca gacatatcgc tcatcacaga tcaacatcac tgctatcacc aacatg        2096

<210> SEQ ID NO 3
<211> LENGTH: 2112
<212> TYPE: DNA
<213> ORGANISM: Fusarium venenatum

<400> SEQUENCE: 3
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg     180
aatgacaaac ctacgggtcc gttcttgaga agtggcctga gatttctcac ttggtgagaa     240
aaaggacggg cgagcgggag cctgagtcag aagaaatacc tgtctccttg gatctcacat     300
gacggtgttg tggaagagtg catctattgt cattgctgga gtgacggcag agtaggggtc     360
taaagaaacc catactgagt agagatggag aagacaacaa aagcccaaga cgacagagac     420
gacagaagat taaagctatc agagcgagac tatatcacta ttcgaaacct gcgagtaatt     480
taacaagaag tacacatcat cattgttatc aattcgacga agacatggtc gaaaattctt     540
gcggtgtata tgtctgttgt atatgggcct gggcattgtt attttcgcc gtctttatgt      600 gtactaacac ttccattgat accccagaac aaagatgaa cgcttaaaca gcaccaaaat      660
caggagaaga atggcgctgc tctaggtatg cttctgggat aaaaagcgat gttgatacct     720
ctcagaaaag aagtgatttg aagttgaatc aaacaaatag ccgatggagc gatctgaagg     780
ggtggcagac ctgctacgcg catttaggca aggcatcaac tcggcagatg attaagaaag     840
gttttgtagg ttcacgtgtt gtgttgtgtt ccattataag tttataacct tgctaagatg     900
caacgactct gacctcaggg tgttagaaaa attgaccact aggagcataa gtgacgaaat     960
tcggggatca agacaataga tagtttcatt ttcatgtgct cctacgtctt ttcacgtaat    1020
gtttcttata aaaaaaaaga tagcattgtc tctttggtga aaagagaaaa aaagatgtta    1080
cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt cttttttta atcaacagaa     1380 acgttccatg ttcatttgtt aatccaatct atttgtgata gcgtttgatg acaaacaata    1440
ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacgggca    1740
actaacgtcc aaaaggcccg aaaaacgtcc atcacgccgc agccgagact tcaatagact    1800
gcacaagaag gaccgatgag atcgaccaga ctaaacccgg gagagtgtca aatatgcggg    1860
ggattgggga acttacccca gaaaagagaa ggaggataaa ttccatgtct ggggttgacg    1920
tctctattgg ttagacacga acgcctgctc tcggcgtaat ttcggccata gcgccaatga    1980
```

```
gggcggaaac tcctgttttg tcaagtcgtc attgttggtt gggtcatgat atatagccag    2040
taggtatccg tcttggtgat tgaccagaca tatcgctcat cacagatcaa catcactgct    2100
atcaccaaca tg                                                        2112

<210> SEQ ID NO 4
<211> LENGTH: 2096
<212> TYPE: DNA
<213> ORGANISM: Fusarium venenatum

<400> SEQUENCE: 4
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg     180
aatgacaaac ctacgggtcc gttcttgaga agtggcctga gatttctcac ttggtgagaa     240
aaaggacggg cgagcgggag cctgagtcag aagaaatacc tgtctccttg gatctcacat     300
gacggtgttg tggaagagtg catctattgt cattgctgga gtgacggcag agtaggggtc     360
taaagaaacc catactgagt agagatggag aagacaacaa agcccaaga cgacagagac      420 gacagaagat taaagctatc agagcgagac tatatcacta ttcgaaacct gcgagtaatt     480
taacaagaag tacacatcat cattgttatc aattcgacga agacatggtc gaaaattctt     540
gcggtgtata tgtctgttgt atatgggcct gggcattgtt atttttcgcc gtctttatgt     600
gtactaacac ttccattgat accccagaac aaaagatgaa cgcttaaaca gcaccaaaat     660
caggagaaga atggcgctgc tctaggtatg cttctgggat aaaaagcgat gttgatacct     720
ctcagaaaag aagtgatttg aagttgaatc aaacaaatag ccgatggagc gatctgaagg     780
ggtggcagac ctgctacgcg catttaggca aggcatcaac tcggcagatg attaagaaag     840
gttttgtagg ttcacgtgtt gtgttgtgtt ccattataag tttataacct tgctaagatg     900
caacgactct gacctcaggg tgttagaaaa attgaccact aggagcataa gtgacgaaat     960 tcgggggatca agacaataga tagtttcatt tcatgtgct cctacgtctt ttcacgtaat    1020
gtttcttata aaaaaaaaga tagcattgtc tctttggtga aaagagaaaa aaagatgtta    1080
cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt ctttttttta atcaacagaa    1380
acgttccatg ttcatttgtt aatccaatct atttgtgata gcgtttgatg acaaacaata    1440
ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacggcca    1740
actaacgtcc aaaaggcccg aaaaacgtcc atcacgccgc agccgagact tcaatagact    1800
gcacaagaag gaccgatgag atcgaccaga ctaaaccatg cggggggattg gggaacttac    1860 cccagaaaag agaaggagga taaattccat gtctgggggtt gacgtctcta ttggttagac    1920
acgaacgcct gctctcggcg taatttcggc catagcgcca atgagggcgg aaactcctgt    1980
```

```
tttgtcaagt cgtcattgtt ggttgggtca tgatatatag ccagtaggta tccgtcttgg    2040
tgattgacca gacatatcgc tcatcacaga tcaacatcac tgctatcacc aacatg        2096

<210> SEQ ID NO 5
<211> LENGTH: 2112
<212> TYPE: DNA
<213> ORGANISM: Fusarium venenatum

<400> SEQUENCE: 5
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg    180
aatgacaaac ctacgggtcc gttcttgaga agtggcctga gatttctcac ttggtgagaa    240
aaaggacggg cgagcgggag cctgagtcag aagaaatacc tgtctccttg gatctcacat    300
gacggtgttg tggaagagtg catctattgt cattgctgga gtgacggcag agtagggggtc   360 taaagaaacc catactgagt agagatggag aagacaacaa agcccaaga cgacagagac     420 gacagaagat taaagctatc agagcgagac tatatcacta ttcgaaacct gcgagtaatt    480
taacaagaag tacacatcat cattgttatc aattcgacga agacatggtc gaaaattctt    540
gcggtgtata tgtctgttgt atatgggcct gggcattgtt attttttcgcc gtctttatgt   600 gtactaacac ttccattgat accccagaac aaaagatgaa cgcttaaaca gcaccaaaat    660
caggagaaga atggcgctgc tctaggtatg cttctgggat aaaaagcgat gttgatacct    720
ctcagaaaag aagtgatttg aagttgaatc aaacaaatag ccgatggagc gatctgaagg    780
ggtggcagac ctgctacgcg catttaggca aggcatcaac tcggcagatg attaagaaag    840
gttttgtagg ttcacgtgtt gtgttgtgtt ccattataag tttataaccct tgctaagatg   900 caacgactct gacctcaggg tgttagaaaa attgaccact aggagcataa gtgacgaaat    960
tcggggatca agacaataga tagtttcatt ttcatgtgct cctacgtctt ttcacgtaat   1020
gtttcttata aaaaaaaaga tagcattgtc tctttggtga aaagagaaaa aaagatgtta   1080
cgacgtgggc ctgattcgaa cagacgcctc cgaagagaat agatttctag tctatcgcgt   1140
tagaccactc cgccaccacg ccttacgtaa tctgtgattg ttgaaagtta ctctcgtgtt   1200
acggtctata cgtgaagaat ctacacttga cgagtctcga ggtctggggt cagttagacg   1260
gaaatgggag aacaaagaga cttggtgaca ttgcaggcaa ccgggtagat gttgaggtca   1320
ttgatcggac aagattgttg cttcaaaagt aacaggtatt ctttttttta atcaacagaa   1380
acgttccatg ttcatttgtt aatccaatct atttgtgata gcgtttgatg acaaacaata   1440
ataatgatgg tctggcggct agtgatcgtt tgtaatgacg tcgtcatata tcctatcact   1500
atacagttgc tttgcacacg cactcacgtc cttcattcgt tgtcttcact atttgatggt   1560
gatttggttc aacaacctac agaaataatg acctgtggtg ttctccgaat atggctagac   1620
caacacaagc ttgtaccgcg gcattcaaat caccatgtga tgcccatcat cagatcatcc   1680 accaaccccaa aaacagacca actactcaca aaaaggcatc tcatcaagaa aaaacgccca  1740
actaacgtcc aaaaggcccg aaaaacgtcc atcacgccgc agccgagact tcaatagact   1800
gcacaagaag gaccgatgag atcgaccaga ctaaacccgg gagagtgtca aatatgcggg   1860 ggattggggga acttaccccca gaaaagagaa ggagggataaa ttccatgtct ggggttgacg  1920
tctctattgg ttagacacga acgcctgctc tcggcgtaat ttcggccata gcgccaatga   1980
```

```
gggcggaaac tcctgttttg tcggcgtaat ttcggccgtt gggtcatgat atatagccag    2040
taggtatccg tcttggtgat tgaccagaca tatcgctcat cacagatcaa catcactgct    2100
atcaccaaca tg                                                        2112

<210> SEQ ID NO 6
<211> LENGTH: 2101
<212> TYPE: DNA
<213> ORGANISM: Fusarium venenatum

<400> SEQUENCE: 6
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg     180
aatgacaaac ctacgggtcc gttcttgaga agtggcctga gatttctcac ttggtgagaa     240
aaaggacggg cgagcgggag cctgagtcag aagaaatacc tgtctccttg gatctcacat     300
gacggtgttg tggaagagtg catctattgt cattgctgga gtgacggcag agtaggggtc     360
taaagaaacc catactgagt agagatggag aagacaacaa agcccaaga cgacagagac      420 gacagaagat taaagctatc agagcgagac tatatcacta ttcgaaacct gcgagtaatt     480
taacaagaag tacacatcat cattgttatc aattcgacga agacatggtc gaaaattctt     540
gcggtgtata tgtctgttgt atatgggcct gggcattgtt attttcgcc gtctttatgt       600 gtactaacac ttccattgat accccagaac aaaagatgaa cgcttaaaca gcaccaaaat     660
caggagaaga atggcgctgc tctaggtatg cttctgggat aaaaagcgat gttgatacct     720
ctcagaaaag aagtgatttg aagttgaatc aaacaaatag ccgatggagc gatctgaagg     780
ggtggcagac ctgctacgcg catttaggca aggcatcaac tcggcagatg attaagaaag    840
gttttgtagg ttcacgtgtt gtgttgtgtt ccattataag tttataaccct tgctaagatg    900 caacgactct gacctcaggg tgttagaaaa attgaccact aggagcataa gtgacgaaat    960
tcggggatca agacaataga tagtttcatt ttcatgtgct cctacgtctt ttcacgtaat   1020
gtttcttata aaaaaaaga tagcattgtc tctttggtga aaagagaaaa aaagatgtta   1080
cgacgtgggc ctgattcgaa cagacgcctc cgaagagaat agatttctag tctatcgcgt   1140
tagaccactc cgccaccacg ccttacgtaa tctgtgattg ttgaaagtta ctctcgtgtt   1200
acggtctata cgtgaagaat ctacacttga cgagtctcga ggtctggggt cagttagacg   1260
gaaatgggag aacaaagaga cttggtgaca ttgcaggcaa ccgggtagat gttgaggtca   1320
ttgatcggac aagattgttg cttcaaaagt aacaggtatt cttttttta atcaacagaa    1380 acgttccatg ttcatttgtt aatccaatct atttgtgata cgtttgatg acaaacaata    1440 ataatgatgg tctggcggct agtgatcgtt tgtaatgacg tcgtcatata tcctatcact   1500
atacagttgc tttgcacacg cactcacgtc cttcattcgt tgtcttcact atttgatggt   1560
gatttggttc aacaacctac agaaataatg acctgtggtg ttctccgaat atggctagac   1620
caacacaagc ttgtaccgcg gcattcaaat caccatgtga tgcccatcat cagatcatcc   1680
accaacccaa aaacagacca actactcaca aaaaggcatc tcatcaagaa aaacggcca    1740 actaacgtcc aaaaggcccg aaaaacgtcc atcacgccgc agccgagact tcaatagact   1800
gcacaagaag gaccgatgag atcgaccaga ctaaacccgg gagagtgtca aatatgcggg   1860
ggattgggga acttacccca gaaaagagaa ggaggataaa ttccatgtct ggggttgacg   1920
tctctattgg ttagacacga acgcctgctc tcggcgtaat ttataccata gcgggaaact   1980
```

-continued

| | |
|---|---|
| cctgttttgt caagtcgtca ttgttggttg ggtcatgata tatagccagt aggtatccgt | 2040 |
| cttggtgatt gaccagacat atcgctcatc acagatcaac atcactgcta tcaccaacat | 2100 |
| g | 2101 |

<210> SEQ ID NO 7
<211> LENGTH: 2109
<212> TYPE: DNA
<213> ORGANISM: Fusarium venenatum

<400> SEQUENCE: 7

| | |
|---|---|
| cctcacccat ctcaacacct gtcgtgtgct cacttgacta cttctttgaa ccagctcgcc | 60 |
| atcggactag tcgaacaagc ttgtcgcccc catacagatg aatgtatgtt taaagctaca | 120 |
| tgatcagcct gaaccgagca taactcgagt gccgagactc ctctgatgta tatcgagatg | 180 |
| aatgacaaac ctacgggtcc gttcttgaga agtggcctga gatttctcac ttggtgagaa | 240 |
| aaaggacggg cgagcgggag cctgagtcag aagaaatacc tgtctccttg gatctcacat | 300 |
| gacggtgttg tggaagagtg catctattgt cattgctgga gtgacggcag agtaggggtc | 360 |
| taaagaaacc catactgagt agagatggag aagacaacaa agcccaaga cgacagagac | 420 |
| gacagaagat taaagctatc agagcgagac tatatcacta ttcgaaacct gcgagtaatt | 480 |
| taacaagaag tacacatcat cattgttatc aattcgacga agacatggtc gaaaattctt | 540 |
| gcggtgtata tgtctgttgt atatgggcct gggcattgtt atttttcgcc gtctttatgt | 600 |
| gtactaacac ttccattgat accccagaac aaaagatgaa cgcttaaaca gcaccaaaat | 660 |
| caggagaaga atggcgctgc tctaggtatg cttctgggat aaaaagcgat gttgatacct | 720 |
| ctcagaaaag aagtgatttg aagttgaatc aaacaaatag ccgatggagc gatctgaagg | 780 |
| ggtggcagac ctgctacgcg catttaggca aggcatcaac tcggcagatg attaagaaag | 840 |
| gttttgtagg ttcacgtgtt gtgttgtgtt ccattataag tttataacct tgctaagatg | 900 |
| caacgactct gacctcaggg tgttagaaaa attgaccact aggagcataa gtgacgaaat | 960 |
| tcggggatca agacaataga tagtttcatt ttcatgtgct cctacgtctt ttcacgtaat | 1020 |
| gtttcttata aaaaaaaga tagcattgtc tctttggtga aaagagaaaa aaagatgtta | 1080 |
| cgacgtgggc ctgattcgaa cagacgcctc cgaagagaat agatttctag tctatcgcgt | 1140 |
| tagaccactc cgccaccacg ccttacgtaa tctgtgattg ttgaaagtta ctctcgtgtt | 1200 |
| acggtctata cgtgaagaat ctacacttga cgagtctcga ggtctggggt cagttagacg | 1260 |
| gaaatgggag aacaaagaga cttggtgaca ttgcaggcaa ccgggtagat gttgaggtca | 1320 |
| ttgatcggac aagattgttg cttcaaaagt aacaggtatt cttttttta atcaacagaa | 1380 |
| acgttccatg ttcatttgtt aatccaatct atttgtgata cgtttgatg acaaacaata | 1440 |
| ataatgatgg tctggcggct agtgatcgtt tgtaatgacg tcgtcatata tcctatcact | 1500 |
| atacagttgc tttgcacacg cactcacgtc cttcattcgt tgtcttcact atttgatggt | 1560 |
| gatttggttc aacaacctac agaaataatg acctgtggtg ttctccgaat atggctagac | 1620 |
| caacacaagc ttgtaccgcg gcattcaaat caccatgtga tgcccatcat cagatcatcc | 1680 |
| accaacccaa aaacagacca actactcaca aaaaggcatc tcatcaagaa aaaacggcca | 1740 |
| actaacgtcc aaaaggcccg aaaaacgtcc atcacgccgc agccgagact tcaatagact | 1800 |
| gcacaagaag gaccgatgag atcgaccaga ctaaacccgg gagagtgtca aatatgcggg | 1860 |
| ggattgggga acttaccccca gaaaagagaa ggaggataaa ttccatgtct ggggttgacg | 1920 |

```
tctctattgg ttagacacga acgcctgctc tcgtaattta taccatagcg ccaatgaggg    1980
cggaaactcc tgttttgtca agtcgtcatt gttggttggg tcatgatata tagccagtag    2040
gtatccgtct tggtgattga ccagacatat cgctcatcac agatcaacat cactgctatc    2100
accaacatg                                                            2109

<210> SEQ ID NO 8
<211> LENGTH: 2112
<212> TYPE: DNA
<213> ORGANISM: Fusarium venenatum

<400> SEQUENCE: 8
cctcacccat ctcaacacct gtcgtgtgct cacttgacta cttctttgaa ccagctcgcc      60
atcggactag tcgaacaagc ttgtcgcccc catacagatg aatgtatgtt taaagctaca    120
tgatcagcct gaaccgagca taactcgagt gccgagactc ctctgatgta tatcgagatg    180
aatgacaaac ctacgggtcc gttcttgaga agtggcctga gatttctcac ttggtgagaa    240
aaaggacggg cgagcgggag cctgagtcag aagaaatacc tgtctccttg gatctcacat    300
gacggtgttg tggaagagtg catctattgt cattgctgga gtgacggcag agtaggggtc    360
taaagaaacc catactgagt agagatggag aagacaacaa aagcccaaga cgacagagac    420
gacagaagat taaagctatc agagcgagac tatatcacta ttcgaaacct gcgagtaatt    480
taacaagaag tacacatcat cattgttatc aattcgacga agacatggtc gaaaattctt    540
gcggtgtata tgtctgttgt atatgggcct gggcattgtt attttcgcc gtctttatgt      600 gtactaacac ttccattgat accccagaac aaaagatgaa cgcttaaaca gcaccaaaat    660
caggagaaga atggcgctgc tctaggtatg cttctgggat aaaaagcgat gttgatacct    720
ctcagaaaag aagtgatttg aagttgaatc aaacaaatag ccgatggagc gatctgaagg    780
ggtggcagac ctgctacgcg catttaggca aggcatcaac tcggcagatg attaagaaag    840
gttttgtagg ttcacgtgtt gtgttgtgtt ccattataag tttataacct tgctaagatg    900
caacgactct gacctcaggg tgttagaaaa attgaccact aggagcataa gtgacgaaat    960
tcggggatca agacaataga tagtttcatt ttcatgtgct cctacgtctt ttcacgtaat    1020
gtttcttata aaaaaaaga tagcattgtc tctttggtga aaagagaaaa aaagatgtta    1080
cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt cttttttta atcaacagaa      1380 acgttccatg ttcatttgtt aatccaatct atttgtgata gcgtttgatg acaaacaata    1440
ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacggcca    1740
actaacgtcc aaaaggcccg aaaaacgtcc atcacgccgc agccgagact tcaatagact    1800
gcacaagaag gaccgatgag atcgaccaga ctaaacccgg gagagtgtca aatatgcggg    1860
ggattgggga acttaccccca gaaaagagaa ggaggataaa ttccatgtct ggggttgacg    1920
```

| | |
|---|---|
| tctctattgg ttagacacga acgcctgctc tcggaaattt aaataccata gcgccaatga | 1980 |
| gggcggaaac tcctgttttg tcaagtcgtc attgttggtt gggtcatgat atatagccag | 2040 |
| taggtatccg tcttggtgat tgaccagaca tatcgctcat cacagatcaa catcactgct | 2100 |
| atcaccaaca tg | 2112 |

```
<210> SEQ ID NO 9
<211> LENGTH: 2112
<212> TYPE: DNA
<213> ORGANISM: Fusarium venenatum

<400> SEQUENCE: 9
```

| | |
|---|---|
| cctcacccat ctcaacacct gtcgtgtgct cacttgacta cttctttgaa ccagctcgcc | 60 |
| atcggactag tcgaacaagc ttgtcgcccc catacagatg aatgtatgtt taaagctaca | 120 |
| tgatcagcct gaaccgagca taactcgagt gccgagactc ctctgatgta tatcgagatg | 180 |
| aatgacaaac ctacgggtcc gttcttgaga agtggcctga gatttctcac ttggtgagaa | 240 |
| aaaggacggg cgagcgggag cctgagtcag aagaaatacc tgtctccttg gatctcacat | 300 |
| gacggtgttg tggaagagtg catctattgt cattgctgga gtgacggcag agtagggggtc | 360 |
| taaagaaacc catactgagt agagatggag aagacaacaa aagcccaaga cgacagagac | 420 |
| gacagaagat taaagctatc agagcgagac tatatcacta ttcgaaacct gcgagtaatt | 480 |
| taacaagaag tacacatcat cattgttatc aattcgacga agacatggtc gaaaattctt | 540 |
| gcggtgtata tgtctgttgt atatgggcct gggcattgtt attttcgcc gtctttatgt | 600 |
| gtactaacac ttccattgat accccagaac aaaagatgaa cgcttaaaca gcaccaaaat | 660 |
| caggagaaga atggcgctgc tctaggtatg cttctgggat aaaaagcgat gttgatacct | 720 |
| ctcagaaaag aagtgatttg aagttgaatc aaacaaatag ccgatggagc gatctgaagg | 780 |
| ggtggcagac ctgctacgcg catttaggca aggcatcaac tcggcagatg attaagaaag | 840 |
| gttttgtagg ttcacgtgtt gtgttgtgtt ccattataag tttataaccct tgctaagatg | 900 |
| caacgactct gacctcaggg tgttagaaaa attgaccact aggagcataa gtgacgaaat | 960 |
| tcggggatca agacaataga tagtttcatt ttcatgtgct cctacgtctt ttcacgtaat | 1020 |
| gtttcttata aaaaaaaaga tagcattgtc tctttggtga aaagagaaaa aaagatgtta | 1080 |
| cgacgtgggc ctgattcgaa cagacgcctc cgaagagaat agatttctag tctatcgcgt | 1140 |
| tagaccactc cgccaccacg ccttacgtaa tctgtgattg ttgaaagtta ctctcgtgtt | 1200 |
| acggtctata cgtgaagaat ctacacttga cgagtctcga ggtctggggt cagttagacg | 1260 |
| gaaatgggag aacaaagaga cttggtgaca ttgcaggcaa ccgggtagat gttgaggtca | 1320 |
| ttgatcggac aagattgttg cttcaaaagt aacaggtatt cttttttta atcaacagaa | 1380 |
| acgttccatg ttcatttgtt aatccaatct atttgtgata gcgtttgatg acaaacaata | 1440 |
| ataatgatgg tctggcggct agtgatcgtt tgtaatgacg tcgtcatata tcctatcact | 1500 |
| atacagttgc tttgcacacg cactcacgtc cttcattcgt tgtcttcact atttgatggt | 1560 |
| gatttggttc aacaacctac agaaataatg acctgtggtg ttctccgaat atggctagac | 1620 |
| caacacaagc ttgtaccgcg gcattcaaat caccatgtga tgcccatcat cagatcatcc | 1680 |
| accaacccaa aaacagacca actactcaca aaaaggcatc tcatcaagaa aaaacggcca | 1740 |
| actaacgtcc aaaaggcccg aaaaacgtcc atcacgccgc agccgagact tcaatagact | 1800 |
| gcacaagaag gaccgatgag atcgaccaga ctaaacccgg gagagtgtca aatatgcggg | 1860 |

```
ggattgggga acttacccca gaaaagagaa ggaggataaa ttccatgtct ggggttgacg    1920
tctctattgg ttagacacga acgcctgctc tcggaaattt aacggccata gcgccaatga    1980
gggcggaaac tcctgttttg tcaagtcgtc attgttggtt gggtcatgat atatagccag    2040
taggtatccg tcttggtgat tgaccagaca tatcgctcat cacagatcaa catcactgct    2100
atcaccaaca tg                                                        2112

<210> SEQ ID NO 10
<211> LENGTH: 2120
<212> TYPE: DNA
<213> ORGANISM: Fusarium venenatum

<400> SEQUENCE: 10
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg     180
aatgacaaac ctacgggtcc gttcttgaga agtggcctga gatttctcac ttggtgagaa     240
aaaggacggg cgagcgggag cctgagtcag aagaaatacc tgtctccttg gatctcacat     300
gacggtgttg tggaagagtg catctattgt cattgctgga gtgacggcag agtaggggtc     360
taaagaaacc catactgagt agagatggag aagacaacaa agcccaaga cgacagagac      420 gacagaagat taaagctatc agagcgagac tatatcacta ttcgaaacct gcgagtaatt     480
taacaagaag tacacatcat cattgttatc aattcgacga agacatggtc gaaaattctt     540
gcggtgtata tgtctgttgt atatgggcct gggcattgtt attttttcgcc gtctttatgt     600 gtactaacac ttccattgat accccagaac aaaagatgaa cgcttaaaca gcaccaaaat     660
caggagaaga atggcgctgc tctaggtatg cttctgggat aaaaagcgat gttgataacct    720 ctcagaaaag aagtgatttg aagttgaatc aaacaaatag ccgatggagc gatctgaagg     780
ggtggcagac ctgctacgcg catttaggca aggcatcaac tcggcagatg attaagaaag     840
gttttgtagg ttcacgtgtt gtgttgtgtt ccattataag tttataaccct tgctaagatg     900 caacgactct gacctcaggg tgttagaaaa attgaccact aggagcataa gtgacgaaat    960
tcggggatca agacaataga tagtttcatt ttcatgtgct cctacgtctt ttcacgtaat    1020
gtttcttata aaaaaaaga tagcattgtc tctttggtga aaagagaaaa aaagatgtta    1080
cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt cttttttta atcaacagaa     1380 acgttccatg ttcattttgtt aatccaatct atttgtgata gcgtttgatg acaaacaata   1440
ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacggcca    1740
actaacgtcc aaaaggcccg aaaaacgtcc atcacgccgc agccgagact tcaatagact    1800
gcacaagaag gaccgatgag atcgaccaga ctaaacccgg gagagtgtca aatatgcggg    1860
```

```
ggattgggga acttacccca gaaaagagaa ggaggataaa ttccatgtct ggggttgacg    1920
tctctattgg ttagacacga acgcctgctc tcggaaattt aaaaatttaa cggccatagc    1980
gccaatgagg gcggaaactc ctgttttgtc aagtcgtcat tgttggttgg gtcatgatat    2040
atagccagta ggtatccgtc ttggtgattg accagacata tcgctcatca cagatcaaca    2100
tcactgctat caccaacatg                                                2120

<210> SEQ ID NO 11
<211> LENGTH: 2112
<212> TYPE: DNA
<213> ORGANISM: Fusarium venenatum

<400> SEQUENCE: 11
cctcacccat ctcaacacct gtcgtgtgct cacttgacta cttctttgaa ccagctcgcc      60
atcggactag tcgaacaagc ttgtcgcccc catacagatg aatgtatgtt taaagctaca     120
tgatcagcct gaaccgagca taactcgagt gccgagactc ctctgatgta tatcgagatg     180
aatgacaaac ctacgggtcc gttcttgaga agtggcctga gatttctcac ttggtgagaa     240
aaaggacggg cgagcgggag cctgagtcag aagaaatacc tgtctccttg gatctcacat     300
gacggtgttg tggaagagtg catctattgt cattgctgga gtgacggcag agtaggggtc     360
taaagaaacc catactgagt agagatggag aagacaacaa aagcccaaga cgacagagac     420
gacagaagat taaagctatc agagcgagac tatatcacta ttcgaaacct gcgagtaatt     480
taacaagaag tacacatcat cattgttatc aattcgacga agacatggtc gaaaattctt     540
gcggtgtata tgtctgttgt atatgggcct gggcattgtt attttttcgcc gtctttatgt     600 gtactaacac ttccattgat accccagaac aaaagatgaa cgcttaaaca gcaccaaaat     660
caggagaaga atggcgctgc tctaggtatg cttctgggat aaaaagcgat gttgatacct     720
ctcagaaaag aagtgatttg aagttgaatc aaacaaatag ccgatgggagc gatctgaagg     780 ggtggcagac ctgctacgcg catttaggca aggcatcaac tcggcagatg attaagaaag     840
gttttgtagg ttcacgtgtt gtgttgtgtt ccattataag tttataacct tgctaagatg     900
caacgactct gacctcaggg tgttagaaaa attgaccact aggagcataa gtgacgaaat     960
tcggggatca agacaataga tagtttcatt ttcatgtgct cctacgtctt ttcacgtaat    1020
gtttcttata aaaaaaaaga tagcattgtc tctttggtga aaagagaaaa aaagatgtta    1080
cgacgtgggc ctgattcgaa cagacgcctc cgaagagaat agatttctag tctatcgcgt    1140
tagaccactc cgccaccacg ccttacgtaa tctgtgattg ttgaaagtta ctctcgtgtt    1200
acggtctata cgtgaagaat ctacacttga cgagtctcga ggtctggggt cagttagacg    1260
gaaatgggag aacaaagaga cttggtgaca ttgcaggcaa ccgggtagat gttgaggtca    1320
ttgatcggac aagattgttg cttcaaaagt aacaggtatt ctttttttta atcaacagaa    1380
acgttccatg ttcatttgtt aatccaatct atttgtgata cgtttgatg acaaacaata    1440 ataatgatgg tctggcggct agtgatcgtt tgtaatgacg tcgtcatata tcctatcact    1500
atacagttgc tttgcacacg cactcacgtc cttcattcgt tgtcttcact atttgatggt    1560
gatttggttc aacaacctac agaaataatg acctgtggtg ttctccgaat atggctagac    1620
caacacaagc ttgtaccgcg gcattcaaat caccatgtga tgcccatcat cagatcatcc    1680
accaacccaa aaacagacca actactcaca aaaaggcatc tcatcaagaa aaaacggcca    1740
actaacgtcc aaaaggcccg aaaaacgtcc atcacgccgc agccgagact tcaatagact    1800
```

| gcacaagaag gaccgatgag atcgaccaga ctaaacccgg gagagtgtca aatatgcggg | 1860 |
| ggattgggga acttacccca gaaaagagaa ggaggataaa ttccatgtct gggggttgacg | 1920 |
| tctctattgg ttagacacga acgcctgctc tattcgtaat ttataccata gcgccaatga | 1980 |
| gggcggaaac tcctgttttg tcaagtcgtc attgttggtt gggtcatgat atatagccag | 2040 |
| taggtatccg tcttggtgat tgaccagaca tatcgctcat cacagatcaa catcactgct | 2100 |
| atcaccaaca tg | 2112 |

<210> SEQ ID NO 12
<211> LENGTH: 2112
<212> TYPE: DNA
<213> ORGANISM: Fusarium venenatum

<400> SEQUENCE: 12

| cctcacccat ctcaacacct gtcgtgtgct cacttgacta cttctttgaa ccagctcgcc | 60 |
| atcggactag tcgaacaagc ttgtcgcccc catacagatg aatgtatgtt taaagctaca | 120 |
| tgatcagcct gaaccgagca taactcgagt gccgagactc ctctgatgta tatcgagatg | 180 |
| aatgacaaac ctacgggtcc gttcttgaga agtggcctga gatttctcac ttggtgagaa | 240 |
| aaaggacggg cgagcgggag cctgagtcag aagaaatacc tgtctccttg gatctcacat | 300 |
| gacggtgttg tggaagagtg catctattgt cattgctgga gtgacggcag agtaggggtc | 360 |
| taaagaaacc catactgagt agagatggag aagcaacaa aagcccaaga cgacagagac | 420 |
| gacagaagat taaagctatc agagcgagac tatatcacta ttcgaaacct gcgagtaatt | 480 |
| taacaagaag tacacatcat cattgttatc aattcgacga agacatggtc gaaaattctt | 540 |
| gcggtgtata tgtctgttgt atatgggcct gggcattgtt attttttcgcc gtctttatgt | 600 |
| gtactaacac ttccattgat accccagaac aaaagatgaa cgcttaaaca gcaccaaaat | 660 |
| caggagaaga atggcgctgc tctaggtatg cttctgggat aaaaagcgat gttgatacct | 720 |
| ctcagaaaag aagtgatttg aagttgaatc aaacaaatag ccgatggagc gatctgaagg | 780 |
| ggtggcagac ctgctacgcg catttaggca aggcatcaac tcggcagatg attaagaaag | 840 |
| gttttgtagg ttcacgtgtt gtgttgtgtt ccattataag tttataacct tgctaagatg | 900 |
| caacgactct gacctcaggg tgttagaaaa attgaccact aggagcataa gtgacgaaat | 960 |
| tcggggatca agacaataga tagtttcatt ttcatgtgct cctacgtctt ttcacgtaat | 1020 |
| gtttcttata aaaaaaaga tagcattgtc tctttggtga aaagagaaaa aaagatgtta | 1080 |
| cgacgtgggc ctgattcgaa cagacgcctc cgaagagaat agatttctag tctatcgcgt | 1140 |
| tagaccactc cgccaccacg ccttacgtaa tctgtgattg ttgaaagtta ctctcgtgtt | 1200 |
| acggtctata cgtgaagaat ctacacttga cgagtctcga ggtctggggt cagttagacg | 1260 |
| gaaatgggag aacaaagaga cttggtgaca ttgcaggcaa ccgggtagat gttgaggtca | 1320 |
| ttgatcggac aagattgttg cttcaaaagt aacaggtatt ctttttttta atcaacagaa | 1380 |
| acgttccatg ttcatttgtt aatccaatct atttgtgata gcgtttgatg acaaacaata | 1440 |
| ataatgatgg tctggcggct agtgatcgtt tgtaatgacg tcgtcatata tcctatcact | 1500 |
| atacagttgc tttgcacacg cactcacgtc cttcattcgt tgtcttcact atttgatggt | 1560 |
| gatttggttc aacaacctac agaaataatg acctgtggtg ttctccgaat atggctagac | 1620 |
| caacacaagc ttgtaccgcg gcattcaaat caccatgtga tgcccatcat cagatcatcc | 1680 |
| accaacccaa aaacagacca actactcaca aaaaggcatc tcatcaagaa aaaacggcca | 1740 |
| actaacgtcc aaaaggcccg aaaaacgtcc atcacgccgc agccgagact tcaatagact | 1800 |

```
gcacaagaag gaccgatgag atcgaccaga ctaaacccgg gagagtgtca aatatgcggg    1860
ggattgggga acttacccca gaaaagagaa ggaggataaa ttccatgtct ggggttgacg    1920
tctctattgg ttagacacga acgcctgctc tcggcgtaat ttataccata gcgaagggtc    1980
tttaggaaac tcctgttttg tcaagtcgtc attgttggtt gggtcatgat atatagccag    2040
taggtatccg tcttggtgat tgaccagaca tatcgctcat cacagatcaa catcactgct    2100
atcaccaaca tg                                                        2112

<210> SEQ ID NO 13
<211> LENGTH: 18
<212> TYPE: DNA
<213> ORGANISM: Fusarium oxysporum

<400> SEQUENCE: 13
atcgagggtg ccaatgtg                                                    18

<210> SEQ ID NO 14
<211> LENGTH: 18
<212> TYPE: DNA
<213> ORGANISM: Fusarium oxysporum

<400> SEQUENCE: 14
gccatttacg acctcagc                                                    18

<210> SEQ ID NO 15
<211> LENGTH: 20
<212> TYPE: DNA
<213> ORGANISM: Fusarium oxysporum

<400> SEQUENCE: 15
ccccgataaa gatggctgta                                                  20

<210> SEQ ID NO 16
<211> LENGTH: 20
<212> TYPE: DNA
<213> ORGANISM: Fusarium oxysporum

<400> SEQUENCE: 16
tcgctaggct cttgggtgac                                                  20

<210> SEQ ID NO 17
<211> LENGTH: 29
<212> TYPE: DNA
<213> ORGANISM: Thermomyces lanuginosus

<400> SEQUENCE: 17
gactcatgag gagctccctt gtgctgttc                                        29

<210> SEQ ID NO 18
<211> LENGTH: 34
<212> TYPE: DNA
<213> ORGANISM: Thermomyces lanuginosus

<400> SEQUENCE: 18
tgattaatta acctaaagac atgtcccaat taac                                  34

<210> SEQ ID NO 19
<211> LENGTH: 26
<212> TYPE: DNA
<213> ORGANISM: Fusarium oxysporum
```

```
<400> SEQUENCE: 19
ggatccttga ataagcgtaa ataggg                                    26

<210> SEQ ID NO 20
<211> LENGTH: 24
<212> TYPE: DNA
<213> ORGANISM: Fusarium oxysporum

<400> SEQUENCE: 20
aagcttgctg agcatttgac tgcc                                      24

<210> SEQ ID NO 21
<211> LENGTH: 20
<212> TYPE: DNA
<213> ORGANISM: Neurospora crassa

<400> SEQUENCE: 21
gtcaggaaac gcagccacac                                           20

<210> SEQ ID NO 22
<211> LENGTH: 20
<212> TYPE: DNA
<213> ORGANISM: Neurospora crassa

<400> SEQUENCE: 22
aggcagccct tggacgacat                                           20

<210> SEQ ID NO 23
<211> LENGTH: 21
<212> TYPE: DNA
<213> ORGANISM: Fusarium oxysporum

<400> SEQUENCE: 23
acaatgttat caatcctctt a                                         21

<210> SEQ ID NO 24
<211> LENGTH: 21
<212> TYPE: DNA
<213> ORGANISM: Fusarium oxysporum

<400> SEQUENCE: 24
tgtcccatgt tctcggtgct a                                         21

<210> SEQ ID NO 25
<211> LENGTH: 23
<212> TYPE: DNA
<213> ORGANISM: Neurospora crassa

<400> SEQUENCE: 25
gccgacgtga caaccaccaa aga                                       23

<210> SEQ ID NO 26
<211> LENGTH: 24
<212> TYPE: DNA
<213> ORGANISM: Neurospora crassa

<400> SEQUENCE: 26
ccacgggatc aggagcagca taaa                                      24

<210> SEQ ID NO 27
<211> LENGTH: 21
<212> TYPE: DNA
<213> ORGANISM: Fusarium oxysporum
```

```
<400> SEQUENCE: 27
gaagcgtcga gatgttcctt g                                              21

<210> SEQ ID NO 28
<211> LENGTH: 19
<212> TYPE: DNA
<213> ORGANISM: Fusarium oxysporum

<400> SEQUENCE: 28
ggcagaccga tgactttgg                                                 19

<210> SEQ ID NO 29
<211> LENGTH: 21
<212> TYPE: DNA
<213> ORGANISM: Thermomyces lanuginosus

<400> SEQUENCE: 29
gttctttgtc tctgcgtgga c                                              21

<210> SEQ ID NO 30
<211> LENGTH: 20
<212> TYPE: DNA
<213> ORGANISM: Thermomyces lanuginosus

<400> SEQUENCE: 30
ggatatccgg aatgttaggc                                                20

<210> SEQ ID NO 31
<211> LENGTH: 31
<212> TYPE: DNA
<213> ORGANISM: Fusarium venenatum

<400> SEQUENCE: 31
cacgaacgcc tgctctatag cgccaatgag g                                   31

<210> SEQ ID NO 32
<211> LENGTH: 31
<212> TYPE: DNA
<213> ORGANISM: Fusarium venenatum

<400> SEQUENCE: 32
cctcattggc gctatagagc aggcgttcgt g                                   31

<210> SEQ ID NO 33
<211> LENGTH: 31
<212> TYPE: DNA
<213> ORGANISM: Fusarium venenatum

<400> SEQUENCE: 33
cgaccagact aaaccatgcg ggggattggg g                                   31

<210> SEQ ID NO 34
<211> LENGTH: 31
<212> TYPE: DNA
<213> ORGANISM: Fusarium venenatum

<400> SEQUENCE: 34
ccccaatccc ccgcatggtt tagtctggtc g                                   31

<210> SEQ ID NO 35
<211> LENGTH: 42
<212> TYPE: DNA
```

<213> ORGANISM: Fusarium venenatum

<400> SEQUENCE: 35
ggcgtaattt ataccatagc gggaaactcc tgttttgtca ag          42

<210> SEQ ID NO 36
<211> LENGTH: 42
<212> TYPE: DNA
<213> ORGANISM: Fusarium venenatum

<400> SEQUENCE: 36
cttgacaaaa caggagtttc cgctatggt ataaattacg cc           42

<210> SEQ ID NO 37
<211> LENGTH: 27
<212> TYPE: DNA
<213> ORGANISM: Fusarium venenatum

<400> SEQUENCE: 37
cgaacgcctg ctctcgtaat ttatacc                           27

<210> SEQ ID NO 38
<211> LENGTH: 27
<212> TYPE: DNA
<213> ORGANISM: Fusarium venenatum

<400> SEQUENCE: 38
ggtataaatt acgagagcag gcgttcg                           27

<210> SEQ ID NO 39
<211> LENGTH: 30
<212> TYPE: DNA
<213> ORGANISM: Fusarium venenatum

<400> SEQUENCE: 39
ctcggcgtaa tttcggccat agcgccaatg                        30

<210> SEQ ID NO 40
<211> LENGTH: 30
<212> TYPE: DNA
<213> ORGANISM: Fusarium venenatum

<400> SEQUENCE: 40
cattggcgct atggccgaaa ttacgccgag                        30

<210> SEQ ID NO 41
<211> LENGTH: 34
<212> TYPE: DNA
<213> ORGANISM: Fusarium venenatum

<400> SEQUENCE: 41
cgcctgctct cggaaattta ataccatag cgcc                    34

<210> SEQ ID NO 42
<211> LENGTH: 34
<212> TYPE: DNA
<213> ORGANISM: Fusarium venenatum

<400> SEQUENCE: 42
ggcgctatgg tatttaaatt tccgagagca ggcg                   34

<210> SEQ ID NO 43
<211> LENGTH: 38

```
<212> TYPE: DNA
<213> ORGANISM: Fusarium venenatum

<400> SEQUENCE: 43
cgcctgctct cggaaattta acggccatag cgccaatg                                   38

<210> SEQ ID NO 44
<211> LENGTH: 38
<212> TYPE: DNA
<213> ORGANISM: Fusarium venenatum

<400> SEQUENCE: 44
cattggcgct atggccgtta aatttccgag agcaggcg                                   38

<210> SEQ ID NO 45
<211> LENGTH: 45
<212> TYPE: DNA
<213> ORGANISM: Fusarium venenatum

<400> SEQUENCE: 45
gcctgctctc ggaaatttaa aaatttaacg gccatagcgc caatg                           45

<210> SEQ ID NO 46
<211> LENGTH: 45
<212> TYPE: DNA
<213> ORGANISM: Fusarium venenatum

<400> SEQUENCE: 46
attggcgcta tggccgttaa attttaaat ttccgagagc aggcg                            45

<210> SEQ ID NO 47
<211> LENGTH: 44
<212> TYPE: DNA
<213> ORGANISM: Fusarium venenatum

<400> SEQUENCE: 47
cgaacgcctg ctcttatatg ccgggcgcaa atagcgccaa tgag                            44

<210> SEQ ID NO 48
<211> LENGTH: 44
<212> TYPE: DNA
<213> ORGANISM: Fusarium venenatum

<400> SEQUENCE: 48
ctcattggcg ctatttgcgc ccggcatata agagcaggcg ttcg                            44

<210> SEQ ID NO 49
<211> LENGTH: 30
<212> TYPE: DNA
<213> ORGANISM: Fusarium venenatum

<400> SEQUENCE: 49
cgaacgcctg ctctattcgt aatttatacc                                            30

<210> SEQ ID NO 50
<211> LENGTH: 30
<212> TYPE: DNA
<213> ORGANISM: Fusarium venenatum

<400> SEQUENCE: 50
ggtataaatt acgaatagag caggcgttcg                                            30

<210> SEQ ID NO 51
```

```
<211> LENGTH: 48
<212> TYPE: DNA
<213> ORGANISM: Fusarium venenatum

<400> SEQUENCE: 51
cgtaatttat accatagcga agggtcttta ggaaactcct gttttgtc          48

<210> SEQ ID NO 52
<211> LENGTH: 48
<212> TYPE: DNA
<213> ORGANISM: Fusarium venenatum

<400> SEQUENCE: 52
gacaaaacag gagtttccta aagacccttc gctatggtat aaattacg          48

<210> SEQ ID NO 53
<211> LENGTH: 39
<212> TYPE: DNA
<213> ORGANISM: Fusarium venenatum

<400> SEQUENCE: 53
ctcctgtttt gtcggcgtaa tttcggccgt tgggtcatg                     39

<210> SEQ ID NO 54
<211> LENGTH: 39
<212> TYPE: DNA
<213> ORGANISM: Fusarium venenatum

<400> SEQUENCE: 54
catgacccaa cggccgaaat tacgccgaca aaacaggag                     39

<210> SEQ ID NO 55
<211> LENGTH: 21
<212> TYPE: DNA
<213> ORGANISM: Fusarium venenatum

<400> SEQUENCE: 55
cgaacagacg cctccgaaga g                                        21

<210> SEQ ID NO 56
<211> LENGTH: 21
<212> TYPE: DNA
<213> ORGANISM: Thermomyces lanuginosus

<400> SEQUENCE: 56
gtgacatcgc ccactccaga g                                        21

<210> SEQ ID NO 57
<211> LENGTH: 21
<212> TYPE: DNA
<213> ORGANISM: Fusarium venenatum

<400> SEQUENCE: 57
gatgttacga cgtgggcctg a                                        21

<210> SEQ ID NO 58
<211> LENGTH: 16
<212> TYPE: DNA
<213> ORGANISM: Fusarium venenatum

<400> SEQUENCE: 58
acgccgcagc cgagac                                              16
```

```
<210> SEQ ID NO 59
<211> LENGTH: 16
<212> TYPE: DNA
<213> ORGANISM: Thermomyces lanuginosus

<400> SEQUENCE: 59
ctggttattg ccgccg                                                   16

<210> SEQ ID NO 60
<211> LENGTH: 21
<212> TYPE: DNA
<213> ORGANISM: Thermomyces lanuginosus

<400> SEQUENCE: 60
taccgcatta cccacaccaa t                                             21

<210> SEQ ID NO 61
<211> LENGTH: 21
<212> TYPE: DNA
<213> ORGANISM: Fusarium oxysporum

<400> SEQUENCE: 61
tgttcggcag acagataact g                                             21

<210> SEQ ID NO 62
<211> LENGTH: 21
<212> TYPE: DNA
<213> ORGANISM: Fusarium venenatum

<400> SEQUENCE: 62
gcccaagacg acagagacga c                                             21

<210> SEQ ID NO 63
<211> LENGTH: 21
<212> TYPE: DNA
<213> ORGANISM: Fusarium venenatum

<400> SEQUENCE: 63
atgacctcaa catctacccg g                                             21

<210> SEQ ID NO 64
<211> LENGTH: 19
<212> TYPE: DNA
<213> ORGANISM: Fusarium venenatum

<400> SEQUENCE: 64
tctggagtgg gcgatgtca                                                19

<210> SEQ ID NO 65
<211> LENGTH: 39
<212> TYPE: DNA
<213> ORGANISM: Fusarium venenatum

<400> SEQUENCE: 65
accagtggac ttgcgggcgt acccatttcc acgcaggtc                          39

<210> SEQ ID NO 66
<211> LENGTH: 39
<212> TYPE: DNA
<213> ORGANISM: Thermomyces lanuginosus

<400> SEQUENCE: 66
gacctgcgtg gaaatgggta cgcccgcaag tccactggt                          39
```

```
<210> SEQ ID NO 67
<211> LENGTH: 20
<212> TYPE: DNA
<213> ORGANISM: Thermomyces lanuginosus

<400> SEQUENCE: 67
ggatggcgca gaggttggtg                                                      20

<210> SEQ ID NO 68
<211> LENGTH: 2096
<212> TYPE: DNA
<213> ORGANISM: Fusarium venenatum

<400> SEQUENCE: 68
cctcacccat ctcaacacct gtcgtgtgct cacttgacta cttctttgaa ccagctcgcc          60
atcggactag tcgaacaagc ttgtcgcccc catacagatg aatgtatgtt taaagctaca         120
tgatcagcct gaaccgagca taactcgagt gccgagactc ctctgatgta tatcgagatg         180
aatgacaaac ctacgggtcc gttcttgaga agtggcctga gatttctcac ttggtgagaa         240
aaaggacggg cgagcgggag cctgagtcag aagaaatacc tgtctccttg gatctcacat         300
gacggtgttg tggaagagtg catctattgt cattgctgga gtgacggcag agtaggggtc         360
taaagaaacc catactgagt agagatggag aagacaacaa agcccaaga cgacagagac          420 gacagaagat taaagctatc agagcgagac tatatcacta ttcgaaacct gcgagtaatt         480
taacaagaag tacacatcat cattgttatc aattcgacga agacatggtc gaaaattctt         540
gcggtgtata tgtctgttgt atatgggcct gggcattgtt attttcgcc gtctttatgt          600 gtactaacac ttccattgat accccagaac aaaagatgaa cgcttaaaca gcaccaaaat         660
caggagaaga atggcgctgc tctaggtatg cttctgggat aaaaagcgat gttgatacct         720
ctcagaaaag aagtgatttg aagttgaatc aaacaaatag ccgatggagc gatctgaagg         780
ggtggcagac ctgctacgcg catttaggca aggcatcaac tcggcagatg attaagaaag         840
gttttgtagg ttcacgtgtt gtgttgtgtt ccattataag tttataacct tgctaagatg         900
caacgactct gacctcaggg tgttagaaaa attgaccact aggagcataa gtgacgaaat         960
tcggggatca agacaataga tagtttcatt ttcatgtgct cctacgtctt ttcacgtaat        1020
gtttcttata aaaaaaaga tagcattgtc tctttggtga aaagagaaaa aaagatgtta        1080
cgacgtgggc ctgattcgaa cagacgcctc cgaagagaat agatttctag tctatcgcgt        1140
tagaccactc cgccaccacg ccttacgtaa tctgtgattg ttgaaagtta ctctcgtgtt        1200
acggtctata cgtgaagaat ctacacttga cgagtctcga ggtctggggt cagttagacg        1260
gaaatgggag aacaaagaga cttggtgaca ttgcaggcaa ccgggtagat gttgaggtca        1320
ttgatcggac aagattgttg cttcaaaagt aacaggtatt cttttttta atcaacagaa        1380 acgttccatg ttcatttgtt aatccaatct atttgtgata gcgtttgatg acaaacaata        1440
ataatgatgg tctggcggct agtgatcgtt tgtaatgacg tcgtcatata tcctatcact        1500
atacagttgc tttgcacacg cactcacgtc cttcattcgt tgtcttcact atttgatggt        1560
gatttggttc aacaacctac agaaataatg acctgtggtg ttctccgaat atggctagac        1620
caacacaagc ttgtaccgcg gcattcaaat caccatgtga tgcccatcat cagatcatcc        1680
accaacccaa aaacagacca actactcaca aaaaggcatc tcatcaagaa aaaacggcca        1740
actaacgtcc aaaaggcccg aaaaacgtcc atcacgccgc agccgagact tcaatagact        1800
gcacaagaag gaccgatgag atcgaccaga ctaaacccgg gagagtgtca aatatgcggg        1860
```

```
ggattgggga acttacccca gaaaagagaa ggaggataaa ttccatgtct ggggttgacg   1920
tctctattgg ttagacacga acgcctgctc tatagcgcca atgagggcgg aaactcctgt   1980
tttgtcaagt cgtcattgtt ggttgggtca tgatatatag ccagtaggta tccgtcttgg   2040
tgattgacca gacatatcgc tcatcacaga tcaacatcac tgctatcacc aacatg       2096

<210> SEQ ID NO 69
<211> LENGTH: 2112
<212> TYPE: DNA
<213> ORGANISM: Fusarium venenatum

<400> SEQUENCE: 69
cctcacccat ctcaacacct gtcgtgtgct cacttgacta cttctttgaa ccagctcgcc     60
atcggactag tcgaacaagc ttgtcgcccc catacagatg aatgtatgtt taaagctaca    120
tgatcagcct gaaccgagca taactcgagt gccgagactc ctctgatgta tatcgagatg    180
aatgacaaac ctacgggtcc gttcttgaga agtggcctga gatttctcac ttggtgagaa    240
aaaggacggg cgagcgggag cctgagtcag aagaaatacc tgtctccttg gatctcacat    300
gacggtgttg tggaagagtg catctattgt cattgctgga gtgacggcag agtaggggtc    360
taaagaaacc catactgagt agagatggag aagacaacaa aagcccaaga cgacagagac    420
gacagaagat taaagctatc agagcgagac tatatcacta ttcgaaacct gcgagtaatt    480
taacaagaag tacacatcat cattgttatc aattcgacga agacatggtc gaaaattctt    540
gcggtgtata tgtctgttgt atatgggcct gggcattgtt atttttcgcc gtctttatgt    600
gtactaacac ttccattgat accccagaac aaaagatgaa cgcttaaaca gcaccaaaat    660
caggagaaga atggcgctgc tctaggtatg cttctgggat aaaaagcgat gttgatacct    720
ctcagaaaag aagtgatttg aagttgaatc aaacaaatag ccgatggagc gatctgaagg    780
ggtggcagac ctgctacgcg catttaggca aggcatcaac tcggcagatg attaagaaag    840
gttttgtagg ttcacgtgtt gtgttgtgtt ccattataag tttataacct tgctaagatg    900
caacgactct gacctcaggg tgttagaaaa attgaccact aggagcataa gtgacgaaat    960
tcggggatca agacaataga tagtttcatt ttcatgtgct cctacgtctt ttcacgtaat   1020
gtttcttata aaaaaaaaga tagcattgtc tctttggtga aaagagaaaa aaagatgtta   1080
cgacgtgggc ctgattcgaa cagacgcctc cgaagagaat agatttctag tctatcgcgt   1140
tagaccactc cgccaccacg ccttacgtaa tctgtgattg ttgaaagtta ctctcgtgtt   1200
acggtctata cgtgaagaat ctacacttga cgagtctcga ggtctggggt cagttagacg   1260
gaaatgggag aacaaagaga cttggtgaca ttgcaggcaa ccgggtagat gttgaggtca   1320
ttgatcggac aagattgttg cttcaaaagt aacaggtatt cttttttta atcaacagaa    1380 acgttccatg ttcatttgtt aatccaatct atttgtgata gcgtttgatg acaaacaata   1440
ataatgatgg tctggcggct agtgatcgtt tgtaatgacg tcgtcatata tcctatcact   1500
atacagttgc tttgcacacg cactcacgtc cttcattcgt tgtcttcact atttgatggt   1560
gatttggttc aacaacctac agaaataatg acctgtggtg ttctccgaat atggctagac   1620
caacacaagc ttgtaccgcg gcattcaaat caccatgtga tgcccatcat cagatcatcc   1680
accaacccaa aaacagacca actactcaca aaaaggcatc tcatcaagaa aaaacggcca   1740
actaacgtcc aaaaggcccg aaaaacgtcc atcacgccgc agccgagact tcaatagact   1800
gcacaagaag gaccgatgag atcgaccaga ctaaacccgg gagagtgtca aatatgcggg   1860
```

```
ggattgggga acttacccca gaaaagagaa ggaggataaa ttccatgtct ggggttgacg    1920
tctctattgg ttagacacga acgcctgctc ttatatgccg ggcgcaaata gcgccaatga    1980
gggcggaaac tcctgttttg tcaagtcgtc attgttggtt gggtcatgat atatagccag    2040
taggtatccg tcttggtgat tgaccagaca tatcgctcat cacagatcaa catcactgct    2100
atcaccaaca tg                                                        2112
```